(12) United States Patent
George et al.

(10) Patent No.: US 11,104,672 B2
(45) Date of Patent: Aug. 31, 2021

(54) POLYMORPHS

(71) Applicant: Syngenta Participations AG, Basel (CH)

(72) Inventors: Neil George, Bracknell (GB); Ian Kevin Jones, Bracknell (GB); John Hone, Bracknell (GB)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/955,497

(22) PCT Filed: Dec. 14, 2018

(86) PCT No.: PCT/EP2018/084957
§ 371 (c)(1),
(2) Date: Jun. 18, 2020

(87) PCT Pub. No.: WO2019/121394
PCT Pub. Date: Jun. 27, 2019

(65) Prior Publication Data
US 2020/0361921 A1      Nov. 19, 2020

(30) Foreign Application Priority Data
Dec. 19, 2017    (GB) ..................................... 1721235

(51) Int. Cl.
*C07D 413/12* (2006.01)
*A01N 43/80* (2006.01)
(52) U.S. Cl.
CPC .......... *C07D 413/12* (2013.01); *A01N 43/80* (2013.01); *C07B 2200/13* (2013.01)
(58) Field of Classification Search
None
See application file for complete search history.

(56) References Cited

U.S. PATENT DOCUMENTS

2014/0243375 A1    8/2014  El Qacemi et al.

FOREIGN PATENT DOCUMENTS

WO    2011067272 A1    6/2011

OTHER PUBLICATIONS

Bullock, Jim et al.: "Crystallisation Science and Agrochemical Formulation", Feb. 4, 2016, Technobis webinar slides.
International Search Report for International application No. PCT/EP2018/084957, dated Apr. 26, 2019.

*Primary Examiner* — Brian J Davis
(74) *Attorney, Agent, or Firm* — BakerHostetler; Toni-Junell Herbert

(57) ABSTRACT

The present invention relates to solid forms of the insecticide of formula (I): compositions comprising the solid forms and methods of their use as insecticides.

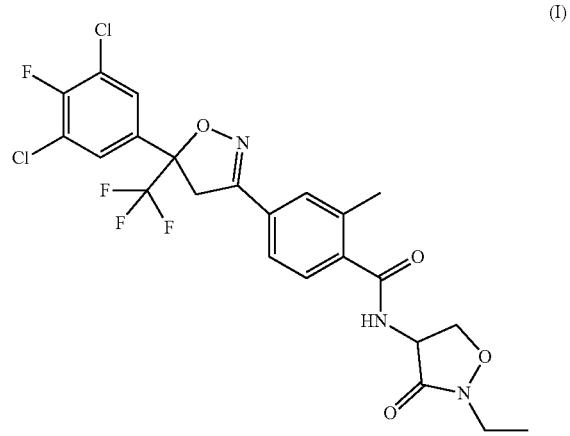

20 Claims, 14 Drawing Sheets

POLYMORPHS

CROSS-REFERENCE TO RELATED APPLICATIONS

This application is a 371 National Stage application of International Application No. PCT/EP2018/084957 filed Dec. 14, 2018 which claims priority to GB 1721235.8, filed Dec. 19, 2017, the entire contents of which applications are hereby incorporated by reference.

This invention relates to solid forms of an isoxazoline derivative, compositions comprising the solid forms and methods of their use as insecticides.

WO 2011/067272 discloses that certain isoxazoline derivatives have pesticidal activity, in particular, insecticidal, acaricidal, molluscicidal and nematicidal activity. In particular, a compound of formula I is disclosed:

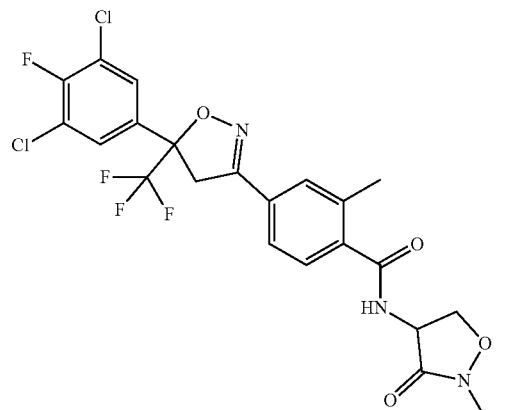
(I)

Mixtures of this compound with other insecticides are disclosed in WO 2012/163960 and with fungicides in WO 2012/163945.

New solid forms of this compound and its isomers, their compositions and methods of their preparation and use have now been discovered.

There are four isomers of the compound of formula I: A, B, C and D, as shown below. The present invention relates to polymorphic forms of all of these isomers, in combination or in isolated form.

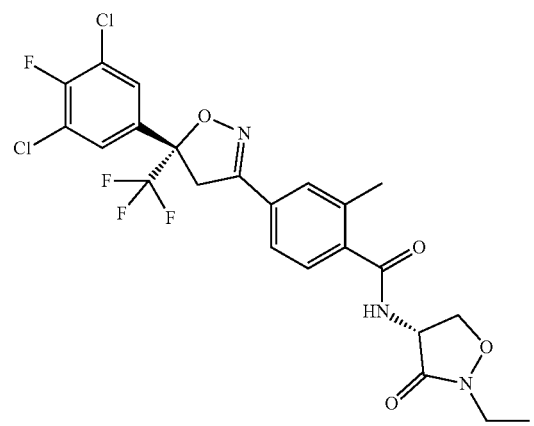
(IA)

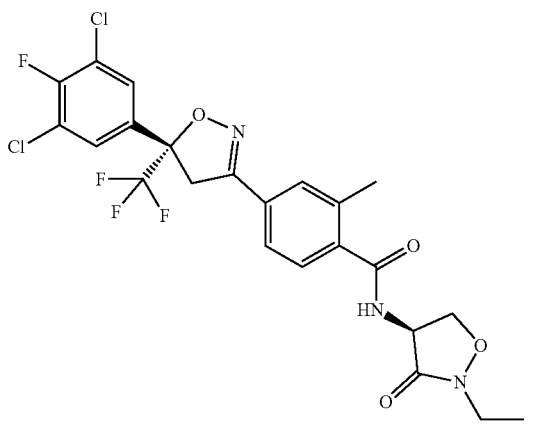
(IB)

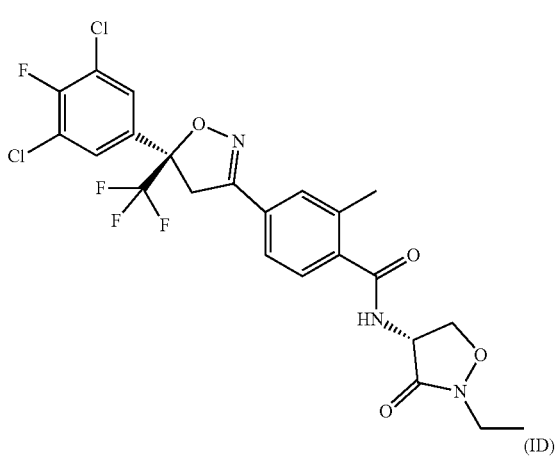
(IC)

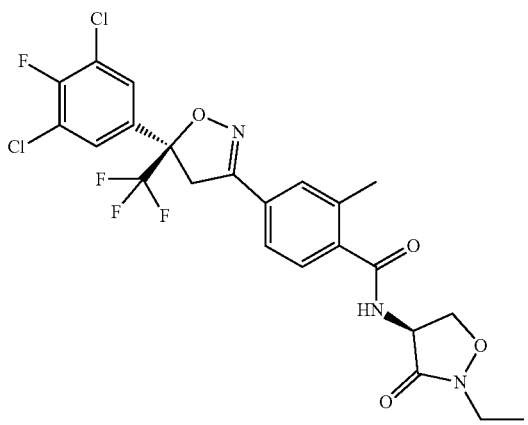
(ID)

Accordingly, the present invention relates to novel crystalline forms of the compound of formula IA, designated Form A(a). This crystalline polymorph Form A(a) may be characterised by the unit cell parameters of its single crystal as shown in Table 1. The polymorph was obtained using the method described in Example 1.

TABLE 1

| Class | Orthorhombic |
|---|---|
| Space Group | $P2_12_12_1$ |
| Cell Lengths (Å) | a = 5.06, b = 18.92, c = 24.17 |

TABLE 1-continued

| Class | Orthorhombic |
|---|---|
| Cell Angles (°) | α = 90, β = 90, γ = 90 |
| Unit Cell Volume (Å$^3$) | 2315 |
| Z | 4 |

In the table, a, b, c=Length of the edges of the unit cell; α, β, γ=Angles of the unit cell; and Z=molecules per cell.

Thus, in one embodiment of the present invention, the crystalline polymorph designated Form A(a) has the following lattice parameters: a=5.06 Å±0.01 Å, b=18.92 Å±0.01 Å, c=24.17 Å±0.01 Å, α=90°±0.01°, β=90°±0.01°, γ=90°±0.01° and volume=2315 Å$^3$±1 Å$^3$.

The crystalline polymorph designated Form A(a) may also be characterised by a powder X-ray diffraction pattern expressed in terms of 2θ angles or d spacings. Thus, in another embodiment of the invention, the crystalline polymorph has a powder X-ray diffraction pattern comprising at least three, at least six, or all 2θ angle values selected from the group consisting of 6.0±0.2, 8.8±0.2, 9.4±0.2, 10.1±0.2, 11.9±0.2, 14.5±0.2, 15.9±0.2, 20.2±0.2, 20.7±0.2, 21.2±0.2, 21.7±0.2, 22.1±0.2 and 22.7±0.2. These peak values, along with the corresponding d spacing values are shown in Table 2 below:

TABLE 2

| 2-Theta | D |
|---|---|
| 6.0 | 14.6 |
| 8.8 | 10.1 |
| 9.4 | 9.4 |
| 10.1 | 8.8 |
| 11.9 | 7.4 |
| 14.5 | 6.1 |
| 15.9 | 5.6 |
| 20.2 | 4.4 |
| 20.7 | 4.3 |
| 21.2 | 4.2 |
| 21.7 | 4.1 |
| 22.1 | 4.0 |
| 22.7 | 3.9 |

These 2θ angle values are derived from a powder X-ray diffraction pattern of the polymorph obtained using the method of Example 1. The values are generated using an average wavelength of 1.54056 Å with a 2θ step size of 0.02°.

In another embodiment, the crystalline polymorph designated Form A(a) has a melting point of 141° C.±2° C. This melting point is obtained using Differential Scanning Calorimetry (DSC) with a heating rate of 10° C./minute.

The crystalline polymorph designated Form A(a) may also be characterised by a Raman spectra expressed in terms of Raman shift (cm$^{-1}$). Thus, in another embodiment of the invention, the crystalline polymorph has a Raman spectra comprising at least three, at least six, at least nine, at least twelve, at least fifteen, or all Raman shift values selected from the group consisting of 1698±2, 1640±2, 1603±2, 1564±2, 1458±2, 1364±2, 1293±2, 1272±2, 1201±2, 1178±2, 1092±2, 1069±2, 1011±2, 926±2, 906±2, 876±2, 833±2, 795±2, 752±2, 721±2, 691±2, 658±2 and 631±2.

The invention also relates to a further novel crystalline form of the compound of formula IA, designated Form A(b) which may be characterised by a powder X-ray diffraction pattern expressed in terms of 2θ angles or d spacings. This crystalline polymorph has a powder X-ray diffraction pattern comprising at least three 2θ angle values selected from the group consisting of 15.3±0.2, 16.3±0.2, 17.6±0.2, 19.3±0.2, 19.8±0.2, 22.0±0.2, 22.9±0.2, 24.9±0.2 and 25.3±0.2. These peak values, along with the corresponding d spacing values are shown in Table 3 below:

TABLE 3

| 2-Theta | D |
|---|---|
| 15.3 | 5.8 |
| 16.3 | 5.4 |
| 17.6 | 5.0 |
| 19.3 | 4.6 |
| 19.8 | 4.5 |
| 22.0 | 4.0 |
| 22.9 | 3.9 |
| 24.9 | 3.6 |
| 25.3 | 3.5 |

These 2θ angle values are derived from a powder X-ray diffraction pattern of the polymorph obtained using the method of Example 1. The values are generated using an average wavelength of 1.54056 Å with a 2θ step size of 0.02°.

The crystalline polymorph designated Form A(b) has a melting point of 152° C.±2° C. This melting point is obtained using Differential Scanning Calorimetry (DSC) with a heating rate of 10° C./minute.

The invention also relates to a further novel crystalline form of the compound of formula IA, designated Form A(h), which is a hydrate. This crystalline polymorph Form A(h) may be characterised by the unit cell parameters of its single crystal as shown in Table 4. The polymorph was obtained using the method described in Example 1.

TABLE 4

| Class | Monoclinic |
|---|---|
| Space Group | P2$_1$ |
| Cell Lengths (Å) | a = 8.03, b = 16.10, c = 20.37 |
| Cell Angles (°) | α = 90, β = 97.02, γ = 90 |
| Unit Cell Volume (Å$^3$) | 2615 |
| Z | 2 |

In the table, a, b, c=Length of the edges of the unit cell; α, β, γ=Angles of the unit cell; and Z=molecules per cell.

Thus, in one embodiment of the present invention, the crystalline polymorph designated Form A(h) has the following lattice parameters: a=8.03 Å±0.01 Å, b=16.10 Å±0.01 Å, c=20.37 Å±0.01 Å, α=90°±0.01°, β=97.02°±0.01°, γ=90°±0.01° and volume=2615 Å$^3$±1 Å$^3$.

The crystalline polymorph designated Form A(h) may also be characterised by a powder X-ray diffraction pattern expressed in terms of 2θ angles or d spacings. Thus, in another embodiment of the invention, the crystalline polymorph has a powder X-ray diffraction pattern comprising at least three, at least six, or all 2θ angle values selected from the group consisting of 4.4±0.2, 7.0±0.2, 8.7±0.2, 10.3±0.2, 11.0±0.2, 12.4±0.2, 12.7±0.2, 13.3±0.2, 14.1±0.2, 15.9±0.2, 17.1±0.2, 18.6±0.2, 19.0±0.2 and 19.6±0.2. These peak values, along with the corresponding d spacing values are shown in Table 5 below:

TABLE 5

| 2-Theta | D |
|---|---|
| 4.4 | 20.2 |
| 7.0 | 12.6 |

TABLE 5-continued

| 2-Theta | D |
| --- | --- |
| 8.7 | 10.1 |
| 10.3 | 8.6 |
| 11.0 | 8.0 |
| 12.4 | 7.1 |
| 12.7 | 7.0 |
| 13.3 | 6.7 |
| 14.1 | 6.3 |
| 15.9 | 5.6 |
| 17.1 | 5.2 |
| 18.6 | 4.8 |
| 19.0 | 4.7 |
| 19.6 | 4.5 |

These 2θ angle values are derived from a powder X-ray diffraction pattern predicted using the single crystal intensity data of the polymorph obtained using the method of Example 1. The values are generated using an average wavelength of 1.54056 Å with a 2θ step size of 0.02°.

Also described is a crystalline form of the compound of formula IA, designated Form A(c) which may be characterized by a melting point of 127° C.±2° C. This melting point is obtained using Differential Scanning Calorimetry (DSC) with a heating rate of 10° C./minute. It is noted that the crystal forms of the compound of formula ID will have identical parameters to those of the compound of formula IA. Therefore, the present invention also relates to novel crystalline forms of the compound of formula ID, which have the physical parameters listed above for the compound of formula IA.

The invention also relates to a novel crystalline form of the compound of formula IB, which may be characterised by a powder X-ray diffraction pattern expressed in terms of 2θ angles or d spacings. This crystalline polymorph has a powder X-ray diffraction pattern comprising at least three 2θ angle values selected from the group consisting of 4.1±0.2, 8.3±0.2, 10.2±0.2, 12.4±0.2, 15.5±0.2, 16.5±0.2, 18.2±0.2, 18.4±0.2, 18.7±0.2, 19.0±0.2, 20.5±0.2, 21.0±0.2 and 21.4±0.2. These peak values, along with the corresponding d spacing values are shown in Table 6 below:

TABLE 6

| 2-Theta | D |
| --- | --- |
| 4.1 | 21.4 |
| 8.3 | 10.7 |
| 10.2 | 8.7 |
| 12.4 | 7.1 |
| 15.5 | 5.7 |
| 16.5 | 5.4 |
| 18.2 | 4.9 |
| 18.4 | 4.8 |
| 18.7 | 4.7 |
| 19.0 | 4.7 |
| 20.5 | 4.3 |
| 21.0 | 4.2 |
| 21.4 | 4.1 |

These 2θ angle values are derived from a powder X-ray diffraction pattern predicted using the single crystal intensity data of the polymorph obtained using the method of Example 1. The values are generated using an average wavelength of 1.54056 Å with a 2θ step size of 0.02°.

The crystalline polymorph of the compound of formula IB has a melting point of 206° C.±2° C. This melting point is obtained using Differential Scanning Calorimetry (DSC) with a heating rate of 10° C./minute.

The invention also relates to a novel crystalline form of the compound of formula IC, which may be characterised by a powder X-ray diffraction pattern expressed in terms of 2θ angles or d spacings. This crystalline polymorph has a powder X-ray diffraction pattern comprising at least three 2θ angle values selected from the group consisting 4.1±0.2, 8.3±0.2, 10.2±0.2, 12.4±0.2, 15.5±0.2, 16.5±0.2, 18.2±0.2, 18.4±0.2, 18.7±0.2, 19.0±0.2, 20.5±0.2, 21.0±0.2 and 21.4±0.2. These peak values, along with the corresponding d spacing values are shown in Table 7 below. It is noted that the powder X-ray diffraction profile of the compound of formula IC is identical to that of the compound of formula IB.

TABLE 7

| 2-Theta | D |
| --- | --- |
| 4.1 | 21.4 |
| 8.3 | 10.7 |
| 10.2 | 8.7 |
| 12.4 | 7.1 |
| 15.5 | 5.7 |
| 16.5 | 5.4 |
| 18.2 | 4.9 |
| 18.4 | 4.8 |
| 18.7 | 4.7 |
| 19.0 | 4.7 |
| 20.5 | 4.3 |
| 21.0 | 4.2 |
| 21.4 | 4.1 |

These 2θ angle values are derived from a powder X-ray diffraction pattern predicted using the single crystal intensity data of the polymorph obtained using the method of Example 1. The values are generated using an average wavelength of 1.54056 Å with a 2θ step size of 0.02°.

The crystalline polymorph of the compound of formula IC has a melting point of 206° C.±2° C. This melting point is obtained using Differential Scanning Calorimetry (DSC) with a heating rate of 10° C./minute.

The invention also relates to a further novel crystalline form of a racemate of the compounds of formula IA and formula ID, which may be characterised by a powder X-ray diffraction pattern expressed in terms of 2θ angles or d spacings. This crystalline polymorph has a powder X-ray diffraction pattern comprising at least three 2θ angle values selected from the group consisting of 4.0±0.2, 8.1±0.2, 9.7±0.2, 11.1±0.2, 12.7±0.2, 15.3±0.2, 15.9±0.2, 16.2±0.2, 16.7±0.2, 18.4±0.2, 19.5±0.2, 19.8±0.2, 20.3±0.2, 21.8±0.2 and 23.9±0.2. These peak values, along with the corresponding d spacing values are shown in Table 8 below:

TABLE 8

| 2-Theta | D |
| --- | --- |
| 4.0 | 21.9 |
| 8.1 | 11.0 |
| 9.7 | 10.2 |
| 11.1 | 8.0 |
| 12.7 | 7.0 |
| 15.3 | 5.8 |
| 15.9 | 5.6 |
| 16.2 | 5.5 |
| 16.7 | 5.3 |
| 18.4 | 4.8 |
| 19.5 | 4.6 |
| 19.8 | 4.5 |
| 20.3 | 4.4 |

TABLE 8-continued

| 2-Theta | D |
|---|---|
| 21.8 | 4.1 |
| 23.9 | 3.7 |

These 2θ angle values are derived from a powder X-ray diffraction pattern of the polymorph obtained using the method of Example 1. The values are generated using an average wavelength of 1.54056 Å with a 2θ step size of 0.02°.

The crystalline polymorph of the racemate of the compounds of formula IA and ID has a melting point of 173° C.±2° C. This melting point is obtained using Differential Scanning Calorimetry (DSC) with a heating rate of 10° C./minute.

In the context of the present invention, a polymorph is a particular crystal form of a chemical compound that can exist in more than one crystal form in the solid state. A crystal form of a compound contains the constituent molecules arranged in orderly repeating patterns extending in all three spatial dimensions (in contrast, an amorphous solid form has no long-range order in the position of molecules). Different polymorphs of a compound have different arrangements of atoms and or molecules in their crystal structure. When the compound is a biologically active compound, such as an insecticide, the difference in crystal structures can lead to different polymorphs having differing chemical, physical and biological properties. Properties which may be affected include crystal shape, density, hardness, colour, chemical stability, melting point, hydroscopicity, suspensibility, dissolution rate and biological availability. As such, a specific polymorph may have properties which make it more advantageous in a particular use relative to another polymorph of the same compound: in particular, the physical, chemical and biological properties listed above can have a significant effect on the development of production methods and formulations, the ease with which a compound can be combined in a formulation with other active ingredients and formulation components and the quality and efficacy of plant treatment agents, such as insecticides. It is noted that predicting whether the solid state of a compound may be present as more than one polymorph is not possible and nor is it possible to predict the properties of any of these crystal forms.

In particular, use of a specific polymorph may allow use of new formulations compared with existing polymorphic/amorphous forms of a compound. This might be advantageous for a number of reasons. For example, a suspension concentrate (SC) formulation may be preferred over an emulsion concentrate (EC) because the lack of solvent in the SC often means that the formulation is likely to be less phytotoxic than an equivalent EC formulation—however, if the existing form of a compound is not stable in such an SC formulations, polymorphic conversion might occur leading to unwanted crystal growth. Such crystal growth is detrimental because it leads to, for example, thickening and potentially solidification of the formulation which can lead to blockages in application equipment, e.g. in spray nozzles in agricultural application machinery. Using a stable polymorphic form would overcome these issues.

Assaying the solid phase for the presence of crystals may be carried out by conventional methods known in the art. For example, it is convenient and routine to use powder X-ray diffraction techniques. Other techniques which may be used include differential scanning calorimetry (DSC), thermogravimetric analysis (TGA) and Raman or Infra-red spectroscopy, NMR, gas chromatography or HPLC. Single crystal X-ray diffraction is especially useful in identifying crystal structures.

The polymorphs of the invention may be applied in unchanged form but are more preferably incorporated into agrochemical compositions by conventional means. Accordingly, in a further aspect, the invention provides an agrochemical composition comprising a polymorph of the invention as defined above and at least one agriculturally acceptable carrier or diluent.

In addition, compositions of the invention may comprise more than one polymorph of the invention. In particular, the compound of formula IA is more biologically active than the compounds of formulas IB, IC and ID. As such, whilst the compositions of the invention may contain a mixture of the compounds of IA, IB, IC and ID in the polymorphic forms disclosed herein or otherwise in any amounts, they may also be enriched for the compound of formula IA or a polymorph of the compound of formula IA. In particular, they may be enriched for the polymorph designated Form A(a). 'Enriched' means that the molar proportion of the compound or polymorph of formula IA compared to the total amount of the compounds of formula IA, IB, IC and ID is greater than 50%, e.g, at least 55, 60, 65, 70, 75, 80, 85, 90, 95, 96, 97, 98 or at least 99%.

The agrochemical compositions comprising the polymorph or polymorphs of the present invention are preventively and/or curatively valuable active ingredients in the field of pest control, even at low rates of application, have a favourable biocidal spectrum and are well tolerated by warm-blooded species, fish and plants. Compositions of the invention may act against all or only individual developmental stages of normally sensitive, but also resistant, animal pests, such as insects or representatives of the order Acarina. The insecticidal or acaricidal activity of the compositions can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

As such, the agrochemical compositions comprising the polymorph or polymorphs of the present invention can be used for the control of plant pathogenic insects on a number of plant species. Accordingly, the invention also provides a method of preventing or controlling insect infection on plants or plant propagation material comprising treating the plant or plant propagation material with an insecticidally effective amount of an agricultural composition of the invention.

The term "insecticide" as used herein means a compound or composition that controls or modifies the growth of insects. The term "insecticidally effective amount" means the quantity of such a compound or composition or a combination of such compounds or compositions that is capable of killing, controlling, or infecting insects, retarding the growth or reproduction of insects, reducing an insect population, and/or reducing damage to plants caused by insects.

By 'plant propagation material' is meant seeds of all kinds (fruit, tubers, bulbs, grains etc.), cuttings, cut shoots and the like.

Examples of the abovementioned animal pests are:
from the order Acarina, for example, *Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp.,*Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp., *Polyphagotarsonemus* spp, *Psoroptes* spp., *Rhipicephalus* spp., *Rhizoglyphus* spp.,*Sarcoptes* spp., *Steneotarsonemus* spp, *Tarsonemus* spp. and *Tetranychus* spp.;

from the order Anoplura, for example, *Haematopinus* spp., *Linognathus* spp., *Pediculus* spp., *Pemphigus* spp. and *Phylloxera* spp.;

from the order Coleoptera, for example, *Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp., *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp., *Sternechus subsignatus*, *Tenebrio* spp., *Tribolium* spp. and *Trogoderma* spp.;

from the order Diptera, for example, *Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example, *Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., and *Vatiga illudens*;

from the order Homoptera, for example, *Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aonidiella auranti*, *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii Scop.*, *Ceroplaster* spp, *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus pini Mats*, *Odonaspis ruthae*, *Oregma lanigera Zehnter*, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp., *Tridiscus sporoboli*, *Trionymus* spp, *Trioza erytreae*, *Unaspis citri*, *Zygina flammigera*, and *Zyginidia scutellaris*;

from the order Hymenoptera, for example, *Acromyrmex*, *Arge* spp, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order Isoptera, for example, *Coptotermes* spp, *Corniternes cumulans*, *Incisitermes* spp, *Macrotermes* spp, *Mastotermes* spp, *Microtermes* spp, *Reticulitermes* spp.; *Solenopsis geminate*;

from the order Lepidoptera, for example, *Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp, *Argyrotaenia* spp., *Autographa* spp., *Bucculatrix thurberiella*, *Busseola fusca*, *Cadra cautella*, *Carposina nipponensis*, *Chilo* spp., *Choristoneura* spp., *Chrysoteuchia topiaria*, *Clysia ambiguella*, *Cnaphalocrocis* spp., *Cnephasia* spp., *Cochylis* spp., *Coleophora* spp., *Colias lesbia*, *Cosmophila flava*, *Crambus* spp, *Crocidolomia binotalis*, *Cryptophlebia leucotreta*, *Cydalima perspectalis*, *Cydia* spp., *Diaphania perspectalis*, *Diatraea* spp., *Diparopsis castanea*, *Earias* spp., *Eldana saccharina*, *Ephestia* spp., *Epinotia* spp, *Estigmene acrea*, *Etiella zinckinella*, *Eucosma* spp., *Eupoecilia ambiguella*, *Euproctis* spp., *Euxoa* spp., *Feltia jaculiferia*, *Grapholita* spp., *Hedya nubiferana*, *Heliothis* spp., *Hellula undalis*, *Herpetogramma* spp., *Hyphantria cunea*, *Keiferia lycopersicella*, *Lasmopalpus lignosellus*, *Leucoptera scitella*, *Lithocollethis* spp., *Lobesia botrana*, *Loxostege bifidalis*, *Lymantria* spp., *Lyonetia* spp., *Malacosoma* spp., *Mamestra brassicae*, *Manduca sexta*, *Mythimna* spp, *Noctua* spp, *Operophtera* spp., *Orniodes indica*, *Ostrinia nubilalis*, *Pammene* spp., *Pandemis* spp., *Panolis flammea*, *Papaipema nebris*, *Pectinophora gossypiela*, *Perileucoptera coffeella*, *Pseudaletia unipuncta*, *Phthorimaea operculella*, *Pieris rapae*, *Pieris* spp., *Plutella xylostella*, *Prays* spp., *Pseudoplusia* spp, *Rachiplusia nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusia ni*, *Tuta absoluta*, and *Yponomeuta* spp.;

from the order Mallophaga, for example, *Damalinea* spp. and *Trichodectes* spp.;

from the order Orthoptera, for example, *Blatta* spp., *Blattella* spp., *Gryllotalpa* spp., *Leucophaea maderae*, *Locusta* spp., *Neocurtilla hexadactyla*, *Periplaneta* spp., *Scapteriscus* spp, and *Schistocerca* spp.;

from the order Psocoptera, for example, *Liposcelis* spp.;

from the order Siphonaptera, for example, *Ceratophyllus* spp., *Ctenocephalides* spp. and *Xenopsylla cheopis*;

from the order Thysanoptera, for example, *Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp; and/or from the order Thysanura, for example, *Lepisma saccharina.*

Examples of soil-inhabiting pests, which can damage a crop in the early stages of plant development, are:

from the order Lepidoptera, for example, *Acleris* spp., *Aegeria* spp., *Agrotis* spp., *Alabama argillaceae, Amylois* spp., *Autographa* spp., *Busseola fusca, Cadra cautella, Chilo* spp., *Crocidolomia binotalis, Diatraea* spp., *Diparopsis castanea, Elasmopalpus* spp., *Heliothis* spp., *Mamestra brassicae, Phthorimaea operculella, Plutella xylostella, Scirpophaga* spp., *Sesamia* spp., *Spodoptera* spp. and *Tortrix* spp.;

from the order Coleoptera, for example, *Agriotes* spp., *Anthonomus* spp., *Atomaria linearis, Chaetocnema tibialis, Conotrachelus* spp., *Cosmopolites* spp., *Curculio* spp., *Dermestes* spp., *Diabrotica* spp., *Dilopoderus* spp., *Epilachna* spp., *Eremnus* spp., *Heteronychus* spp., *Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitotroga* spp., *Somaticus* spp., *Tanymecus* spp., *Tenebrio* spp., *Tribolium* spp., *Trogoderma* spp. and *Zabrus* spp.;

from the order Orthoptera, for example, *Gryllotalpa* spp.;

from the order Isoptera, for example, *Reticulitermes* spp.;

from the order Psocoptera, for example, *Liposcelis* spp.;

from the order Anoplura, for example, *Haematopinus* spp., *Linognathus* spp., *Pediculus* spp., *Pemphigus* spp. and *Phylloxera* spp.;

from the order Homoptera, for example, *Eriosoma larigerum;* from the order Hymenoptera, for example, *Acromyrmex, Atta* spp., *Cephus* spp., *Lasius* spp., *Monomorium pharaonis, Neodiprion* spp., *Solenopsis* spp. and *Vespa* spp.;

from the order Diptera, for example, *Tipula* spp.;

crucifer flea beetles (*Phyllotreta* spp.), root maggots (*Delia* spp.), cabbage seedpod weevil (*Ceutorhynchus* spp.) and aphids.

The compositions of the invention may also be useful for the control of nematodes. As such, the agrochemical compositions comprising the polymorph of the present invention can be used for the control of plant pathogenic nematodes on a number of plant species. Accordingly, the invention also provides a method of controlling damage to plant and parts thereof by plant parasitic nematodes (Endoparasitic-, Semiendoparasitic- and Ectoparasitic nematodes), the method comprising treating the plant or plant propagation material with a nematicidally effective amount of an agricultural composition of the invention.

The term "nematicide" as used herein means a compound or composition that controls or modifies the growth of nematodes. The term "nematicidally effective amount" means the quantity of such a compound or composition or a combination of such compounds or compositions that is capable of killing, controlling, or infecting nematodes, retarding the growth or reproduction of nematodes, reducing a nematode population, and/or reducing damage to plants caused by nematodes.

Examples of the abovementioned plant parasitic nematodes are:

root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Eelonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina,* spp *Hypsoperine* spp., *Macroposthonia* spp., *Melinius* spp., *Punctodera* spp., and *Quinisulcius* spp.

In particular, the nematode species *Meloidogyne* spp., *Heterodera* spp., *Rotylenchus* spp. and *Pratylenchus* spp. can be controlled by the compositions of the invention.

The compositions according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis, Anthemis* spp., *Antirrhinum* spp., *Aster* spp., *Begonia* spp. (e.g. *B. elatior, B.*

*semperflorens, B. tubéreux), Bougainvillea* spp., *Brachycome* spp., *Brassica* spp. (ornamental), *Calceolaria* spp., *Capsicum annuum, Catharanthus roseus, Canna* spp., *Centaurea* spp., *Chrysanthemum* spp., *Cineraria* spp. (*C. maritime), Coreopsis* spp., *Crassula coccinea, Cuphea ignea, Dahlia* spp., *Delphinium* spp., *Dicentra spectabilis, Dorotheanthus* spp., *Eustoma grandiflorum, Forsythia* spp., *Fuchsia* spp., *Geranium gnaphalium, Gerbera* spp., *Gomphrena globosa, Heliotropium* spp., *Helianthus* spp., *Hibiscus* spp., *Hortensia* spp., *Hydrangea* spp., *Hypoestes phyllostachya, Impatiens* spp. (*I. Walleriana), Iresines* spp., *Kalanchoe* spp., *Lantana camara, Lavatera trimestris, Leonotis leonurus, Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum, P. Zonale), Viola* spp. (pansy), *Petunia* spp., *Phlox* spp., *Plecthranthus* spp., *Poinsettia* spp., *Parthenocissus* spp. (*P. quinquefolia, P. tricuspidata), Primula* spp., *Ranunculus* spp., *Rhododendron* spp., *Rosa* spp. (rose), *Rudbeckia* spp., *Saintpaulia* spp., *Salvia* spp., *Scaevola aemola, Schizanthus wisetonensis, Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum), Anthriscus cerefolium, Apium graveolus, Asparagus officinalis, Beta vulgarus, Brassica* spp. (*B. Oleracea, B. Pekinensis, B. rapa), Capsicum annuum, Cicer arietinum, Cichorium endivia, Cichorum* spp. (*C. intybus, C. endivia), Citrillus lanatus, Cucumis* spp. (*C. sativus, C. melo), Cucurbita* spp. (*C. pepo, C. maxima), Cyanara* spp. (*C. scolymus, C. cardunculus), Daucus carota, Foeniculum vulgare, Hypericum* spp., *Lactuca sativa, Lycopersicon* spp. (*L. esculentum, L. lycopersicum), Mentha* spp., *Ocimum basilicum, Petroselinum crispum, Phaseolus* spp. (*P. vulgaris, P. coccineus), Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusta, V. eriocarpa*) and *Vicia faba.*

Preferred ornamental species include African violet, *Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia,* rosemary, sage, St. Johnswort, mint, sweet pepper, tomato and cucumber.

The polymorphs according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The polymorphs according to the invention are further especially suitable for controlling *Mamestra* (preferably in vegetables), *Cydia* (preferably in apples), *Empoasca* (preferably in vegetables, vineyards), *Leptinotarsa* (preferably in potatoes) and *Chilo supressalis* (preferably in rice).

Crops are to be understood as being those which are naturally occurring, obtained by conventional methods of breeding, or obtained by genetic engineering. They include crops which contain so-called output traits (e.g. improved storage stability, higher nutritional value and improved flavour).

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®.

Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents. A further object of the invention is therefore a substrate selected from nonwoven and fabric material comprising a composition which contains a compound of formula (I).

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO 2006/128870, EP 1724392, WO2005113886 or WO 2007/090739.

Further areas of use of the compositions according to the invention are the field of tree injection/trunk treatment for all ornamental trees as well all sort of fruit and nut trees.

In the field of tree injection/trunk treatment, the polymorphs according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |

TABLE B-continued

Examples of native woodborers of economic importance.

| Family | Species | Host or Crop Infested |
|---|---|---|
| | *Oberea ocellata* | Sumac, Apple, Peach, Plum, Pear, Currant, Blackberry |
| | *Oberea tripunctata* | Dogwood, Viburnum, Elm, Sourwood, Blueberry, Rhododendron, Azalea, Laurel, Poplar, Willow, Mulberry |
| | *Oncideres cingulata* | Hickory, Pecan, Persimmon, Elm, Sourwood, Basswood, Honeylocust, Dogwood, Eucalyptus, Oak, Hackberry, Maple, Fruit trees |
| | *Saperda calcarata* | Poplar |
| | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
| | *Dendroctonus frontalis* | Pine |
| | *Dryocoetes betulae* | Birch, Sweetgum, Wild cherry, Beech, Pear |
| | *Monarthrum fasciatum* | Oak, Maple, Birch, Chestnut, Sweetgum, Blackgum, Poplar, Hickory, Mimosa, Apple, Peach, Pine |
| | *Phloeotribus liminaris* | Peach, Cherry, Plum, Black cherry, Elm, Mulberry, Mountain-ash |
| | *Pseudopityophthorus pruinosus* | Oak, American beech, Black cherry, Chickasaw plum, Chestnut, Maple, Hickory, Hornbeam, Hophornbeam |
| Sesiidae | *Paranthrene simulans* | Oak, American chestnut |
| | *Sannina uroceriformis* | Persimmon |
| | *Synanthedon exitiosa* | Peach, Plum, Nectarine, Cherry, Apricot, Almond, Black cherry |
| | *Synanthedon pictipes* | Peach, Plum, Cherry, Beach, Black Cherry |
| | *Synanthedon rubrofascia* | Tupelo |
| | *Synanthedon scitula* | Dogwood, Pecan, Hickory, Oak, Chestnut, Beech, Birch, Black cherry, Elm, Mountain-ash, Viburnum, Willow, Apple, Loquat, Ninebark, Bayberry |
| | *Vitacea polistiformis* | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass ataenius, *A. spretulus*), *Maladera* spp.

(e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family) and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp., Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis*, *Periplaneta americana*, *Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus*, *Chlorophorus pilosis*, *Anobium punctatum*, *Xestobium rufovillosum*, *Ptilinuspecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthesrugicollis*, *Xyleborus* spec., *Tryptodendron* spec., *Apate monachus*, *Bostrychus capucins*, *Heterobostrychus brunneus*, *Sinoxylon* spec. and *Dinoderus minutus*, and also hymenopterans such as *Sirex juvencus*, *Urocerus gigas*, *Urocerus gigas taignus* and *Urocerus augur*, and termites such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis* and *Coptotermes formosanus*, and bristletails such as *Lepisma saccharina*.

The rate at which the agrochemical compositions of the invention are applied will depend upon the particular type of insect etc. to be controlled, the degree of control required and the timing and method of application and can be readily determined by the person skilled in the art. In general, the compositions of the invention can be applied at an application rate of between 0.005 kilograms/hectare (kg/ha) and about 5.0 kg/ha, based on the total amount of active ingredient (wherein 'active ingredient' means the polymorph or polymorphs of the invention) in the composition. An application rate of between about 0.1 kg/ha and about 1.5 kg/ha is preferred, with an application rate of between about 0.3 kg/ha and 0.8 kg/ha being especially preferred.

In practice, the agrochemical compositions comprising the polymorph or polymorphs of the invention are applied as a formulation containing the various adjuvants and carriers known to or used in the industry.

These formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the polymorph or polymorphs ('active ingredient') with the formulation adjuvants in order to obtain formulations in the form of finely divided solids, granules, solutions, dispersions or emulsions. The active ingredient can also be formulated with other adjuvants, such as finely divided solids, mineral oils, oils of vegetable or animal origin, modified oils of vegetable or animal origin, organic solvents, water, surface-active substances or combinations thereof.

The active ingredient can also be contained in very fine microcapsules. Microcapsules contain the active ingredient in a porous carrier. This enables the active ingredient to be released into the environment in controlled amounts (e.g. slow-release). Microcapsules usually have a diameter of from 0.1 to 500 microns. They contain the active ingredient in an amount of about from 25 to 95% by weight of the capsule weight. The active ingredient can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the formulations according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecyl-benzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The formulations according to the invention can include an additive comprising an oil of vegetable or animal origin, a mineral oil, alkyl esters of such oils or mixtures of such oils and oil derivatives. The amount of oil additive in the formulations according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The inventive formulations generally comprise from 0.1 to 99% by weight, especially from 0.1 to 95% by weight, of polymorphs of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline the polymorphs of the invention may be applied at a rate of from 1 to 2000 l/ha, especially from 10 to 1000 l/ha.

Preferred formulations can have the following compositions (weight %):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%

Wettable Powders:

active ingredient: 0.5 to 90%, preferably 1 to 80% surface-active agent: 0.5 to 20%, preferably 1 to 15% solid carrier: 5 to 95%, preferably 15 to 90%

Granules:

active ingredient: 0.1 to 30%, preferably 0.1 to 15% solid carrier: 99.5 to 70%, preferably 97 to 85%

The following Examples further illustrate, but do not limit, the invention.

| Wettable powders | a) | b) | c) |
|---|---|---|---|
| active ingredient | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredient | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| active ingredient | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| active ingredient | 15% |
| sodium lignosulfonate | 2% |
| Carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| active ingredient | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

| Suspension concentrate | |
|---|---|
| active ingredient | 40% |
| propylene glycol | 10% |
| nonylphenol polyethylene glycol ether (15 mol of ethylene oxide) | 6% |
| Sodium lignosulfonate | 10% |
| Carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the active ingredient are mixed with 2 parts of an aromatic solvent and 7 parts of toluene diisocyanate/polymethylene-polyphenylisocyanate-mixture (8:1). This mixture is emulsified in a mixture of 1.2 parts of polyvinyl-alcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredient. The medium capsule diameter is 8-15 microns. The resulting formulation is applied to seeds as an aqueous suspension in an apparatus suitable for that purpose.

Each of the above formulations can be prepared as a package containing the polymorph or polymorphs of the invention together with other ingredients of the formulation (diluents, emulsifiers, surfactants, etc.). The formulations can also be prepared by a tank mix method, in which the ingredients are obtained separately and combined at the grower site.

These formulations can be applied to the areas where control is desired by conventional methods. Dust and liquid formulations, for example, can be applied by the use of power-dusters, broom and hand sprayers and spray dusters. The formulations can also be applied from airplanes as a dust or a spray or by rope wick applications. Both solid and liquid formulations may also be applied to the soil in the locus of the plant to be treated allowing the active ingredient to penetrate the plant through the roots.

The polymorphs of the invention and compositions thereof are also be suitable for the protection of plant propagation material, for example seeds, such as fruit, tubers or kernels, or nursery plants, against pests of the abovementioned type. The propagation material can be treated with the polymorph prior to planting, for example seed can be treated prior to sowing. Alternatively, the polymorph can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a polymorph of the invention. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

Suitably, the agrochemical compositions and formulations of the present invention are applied prior to disease development. Rates and frequency of use of the formulations are those conventionally used in the art and will depend on the risk of infestation by the insect pathogen.

The activity of compositions comprising compounds and polymorphs according to the invention can be broadened considerably, and adapted to prevailing circumstances, by including other active substances. The active substances can be of chemical or biological in type, and in the case of biological could be further modified from the biological species derived in nature. Active substances include substances that control, repel or attract pests that damage or harm useful plants in general, but also substances that improve the growth of a useful plant, such as plant growth regulators, and substances that improve the performance of the active substance, such as synergists. Examples are insecticides, acaricides, nematicides, molluscicides, aligicides, virusicides, rodenticide, bactericides, fungicides, chemosterilants, anthelmintics. Examples of a biological active substance include baculovirus, plant extract, and bacteria.

Accordingly, the present invention provides for the use of a composition according to the present invention together with one or more pesticides, plant nutrients or plant fertilizers. The combination may also encompass specific plant traits incorporated into the plant using any means, for example conventional breeding or genetic modification.

The mixtures of the polymorphs of the invention with other active substances may also have further surprising advantages which can also be described, in a wider sense, as synergistic activity. For example, better tolerance by plants, reduced phytotoxicity, insects can be controlled in their different development stages, or better behaviour relating to production, for example grinding or mixing, storage or use.

Individual active substances can occur in more than one group or class, and at more than one place within a group or class: information about the active substances, their spectrum, sources and classifications can be found from Compendium of Pesticide Common Names (see http://www.alanwood.net/pesticides/index.html) or from the Pesticide Manual created by the British Crop Production Counci (see http://bcpcdata.com/pesticide-manual.html).

Preferred mixtures are indicated below where the polymorph or polymorphs of of the invention are indicated as "I":

Compositions comprising an adjuvant include I+compounds selected from the group of substances consisting of petroleum oils.

Compositions comprising an acaricide include I+1,1-bis (4-chlorophenyl)-2-ethoxyethanol, I+2,4-dichlorophenyl benzenesulfonate, I+2-fluoro-N-methyl-N-1-naphthylacetamide, I+4-chlorophenyl phenyl sulfone, I+abamectin, I+acequinocyl, I+acetoprole, I+acrinathrin, I+aldicarb, I+aldoxycarb, I+alpha-cypermethrin, I+amidithion, I+amidoflumet, I+amidothioate, I+amiton, I+amiton hydrogen oxalate, I+amitraz, I+aramite, I+arsenous oxide, I+AVI 382, I+AZ 60541, I+azinphos-ethyl, I+azinphos-methyl, I+azobenzene, I+azocyclotin, I+azothoate, I+benomyl, I+benoxafos, I+benzoximate, I+benzyl benzoate, I+bifenazate, I+bifenthrin, I+binapacryl, I+brofenvalerate, I+bromocyclen, I+bromophos, I+bromophos-ethyl, I+bromopropylate, I+buprofezin, I+butocarboxim, I+butoxycarboxim, I+butylpyridaben, I+calcium polysulfide, I+camphechlor, I+carbanolate, I+carbaryl, I+carbofuran, I+carbophenothion, I+CGA 50'439, I+chinomethionat, I+chlorbenside, I+chlordimeform, I+chlordimeform hydrochloride, I+chlorfenapyr, I+chlorfenethol, I+chlorfenson, I+chlorfensulfide, I+chlorfenvinphos, I+chlorobenzilate, I+chloromebuform, I+chloromethiuron, I+chloropropylate, I+chlorpyrifos, I+chlorpyrifos-methyl, I+chlorthiophos, I+cinerin I, I+cinerin II, I+cinerins, I+clofentezine, I+closantel, I+coumaphos, I+crotamiton, I+crotoxyphos, I+cufraneb, I+cyanthoate, I+cyflumetofen, I+cyhalothrin, I+cyhexatin, I+cypermethrin, I+DCPM, I+DDT, I+demephion, I+demephion-O, I+demephion-S, I+demeton, I+demeton-methyl, I+demeton-O, I+demeton-O-methyl, I+demeton-S, I+demeton-S-methyl, I+demeton-S-methylsulfon, I+diafenthiuron, I+dialifos, I+diazinon, I+dichlofluanid, I+dichlorvos, I+dicliphos, I+dicofol, I+dicrotophos, I+dienochlor, I+dimefox, I+dimethoate, I+dinactin, I+dinex, I+dinex-diclexine, I+dinobuton, I+dinocap, I+dinocap-4, I+dinocap-6, I+dinocton, I+dinopenton, I+dinosulfon, I+dinoterbon, I+dioxathion, I+diphenyl sulfone, I+disulfiram, I+disulfoton, I+DNOC, I+dofenapyn, I+doramectin, I+endosulfan, I+endothion, I+EPN, I+eprinomectin, I+ethion, I+ethoate-methyl, I+etoxazole, I+etrimfos, I+fenazaflor, I+fenazaquin, I+fenbutatin oxide, I+fenothiocarb, I+fenpropathrin, I+fenpyrad, I+fenpyroximate, I+fenson, I+fentrifanil, I+fenvalerate, I+fipronil, I+fluacrypyrim, I+fluazuron, I+flubenzimine, I+flucycloxuron, I+flucythrinate, I+fluenetil, I+flufenoxuron, I+flumethrin, I+fluorbenside, I+fluvalinate, I+FMC 1137, I+formetanate, I+formetanate hydrochloride, I+formothion, I+formparanate, I+gamma-HCH, I+glyodin, I+halfenprox, I+heptenophos, I+hexadecyl cyclopropanecarboxylate, I+hexythiazox, I+iodomethane, I+isocarbophos, I+isopropyl O-(methoxyaminothiophosphoryl)salicylate, I+ivermectin, I+jasmolin I, I+jasmolin II, I+jodfenphos, I+lindane, I+lufenuron, I+malathion, I+malonoben, I+mecarbam, I+mephosfolan, I+mesulfen, I+methacrifos, I+methamidophos, I+methidathion, I+methiocarb, I+methomyl, I+methyl bromide, I+metolcarb, I+mevinphos, I+mexacarbate, I+milbemectin, I+milbemycin oxime, I+mipafox, I+monocrotophos, I+morphothion, I+moxidectin, I+naled, I+NC-184, I+NC-512, I+nifluridide, I+nikkomycins, I+nitrilacarb, I+nitrilacarb 1:1 zinc chloride complex, I+NNI-0101, I+NNI-0250, I+omethoate, I+oxamyl, I+oxydeprofos, I+oxydisulfoton, I+pp'-DDT, I+parathion, I+permethrin, I+petroleum oils, I+phenkapton, I+phenthoate, I+phorate, I+phosalone, I+phosfolan, I+phosmet, I+phosphamidon, I+phoxim, I+pirimiphos-methyl, I+polychloroterpenes, I+polynactins, I+proclonol, I+profenofos, I+promacyl, I+propargite, I+propetamphos, I+propoxur, I+prothidathion, I+prothoate, I+pyrethrin I, I+pyrethrin II, I+pyrethrins, I+pyridaben, I+pyridaphenthion, I+pyrimidifen, I+pyrimitate, I+quinalphos, I+quintiofos, I+R-1492, I+RA-17, I+rotenone, I+schradan, I+sebufos, I+selamectin, I+SI-0009, I+sophamide, I+spirodiclofen, I+spiromesifen, I+SSI-121, I+sulfiram, I+sulfluramid, I+sulfotep, I+sulfur, I+SZI-121, I+tau-fluvalinate, I+tebufenpyrad, I+TEPP, I+terbam, I+tetrachlorvinphos, I+tetradifon, I+tetranactin, I+tetrasul, I+thiafenox, I+thiocarboxime, I+thiofanox, I+thiometon, I+thioquinox, I+thuringiensin, I+triamiphos, I+triarathene, I+triazophos, I+triazuron, I+trichlorfon, I+trifenofos, I+trinactin, I+vamidothion, I+vaniliprole and I+YI-5302.

Compositions comprising an anthelmintic include I+abamectin, I+crufomate, I+doramectin, I+emamectin, I+emamectin benzoate, I+eprinomectin, I+ivermectin, I+milbemycin oxime, I+moxidectin, I+piperazine, I+selamectin, I+spinosad and I+thiophanate.

Compositions comprising an avicide include I+chloralose, I+endrin, I+fenthion, I+pyridin-4-amine and I+strychnine Compositions comprising a biological control agent include I+*Adoxophyes orana* GV, I+*Agrobacterium radiobacter*, I+*Amblyseius* spp., I+*Anagrapha falcifera* NPV, I+*Anagrus atomus*, I+*Aphelinus abdominalis*, I+*Aphidius colemani*, I+*Aphidoletes aphidimyza*, I+*Autographa californica* NPV, I+*Bacillus firmus*, I+*Bacillus sphaericus* Neide, I+*Bacillus thuringiensis* Berliner, I+*Bacillus thuringiensis* subsp. *aizawai*, I+*Bacillus thuringiensis* subsp. *israelensis*, I+*Bacillus thuringiensis* subsp. *japonensis*, I+*Bacillus thuringiensis* subsp. *kurstaki*, I+*Bacillus thuringiensis* subsp. *tenebrionis*, I+*Beauveria bassiana*, I+*Beauveria brongniartii*, I+*Chrysoperla carnea*, I+*Cryptolaemus montrouzieri*, I+*Cydia pomonella* GV, I+*Dacnusa sibirica*, I+*Diglyphus isaea*, I+*Encarsia formosa*, I+*Eretmocerus eremicus*, I+*Helicoverpa zea* NPV, I+*Heterorhabditis bacteriophora* and *H. megidis*, I+*Hippodamia convergens*, I+*Leptomastix dactylopii*, I+*Macrolophus caliginosus*, I+*Mamestra brassicae* NPV, I+*Metaphycus helvolus*, I+*Metarhizium anisopliae* var. *acridum*, I+*Metarhizium anisopliae* var. *anisopliae*, I+*Neodiprion sertifer* NPV and *N. lecontei* NPV, I+*Orius* spp., I+*Paecilomyces fumosoroseus*, I+*Phytoseiulus persimilis*, I+*Spodoptera exigua* multicapsid nuclear polyhedrosis virus, I+*Steinernema bibionis*, I+*Steinernema carpocapsae*, I+*Steinernema feltiae*, I+*Steinernema glaseri*, I+*Steinernema riobrave*, I+*Steinernema riobravis*, I+*Steinernema scapterisci*, I+*Steinernema* spp., I+*Trichogramma* spp., I+*Typhlodromus occidentalis* and I+*Verticillium lecanii*.

Compositions comprising a soil sterilant include I+iodomethane and methyl bromide.

Compositions comprising a chemosterilant include I+apholate, I+bisazir, I+busulfan, I+diflubenzuron, I+dimatif, I+hemel, I+hempa, I+metepa, I+methiotepa, I+methyl apholate, I+morzid, I+penfluron, I+tepa, I+thiohempa, I+thiotepa, I+tretamine and I+uredepa.

Compositions comprising an insect pheromone include I+(E)-dec-5-en-1-yl acetate with (E)-dec-5-en-1-ol, I+(E)-tridec-4-en-1-yl acetate, I+(E)-6-methylhept-2-en-4-ol, I+(E,Z)-tetradeca-4,10-dien-1-yl acetate, I+(Z)-dodec-7-en-1-yl acetate, I+(Z)-hexadec-11-enal, I+(Z)-hexadec-11-en-1-yl acetate, I+(Z)-hexadec-13-en-11-yn-1-yl acetate, I+(Z)-icos-13-en-10-one, I+(Z)-tetradec-7-en-1-al, I+(Z)-tetradec-9-en-1-ol, I+(Z)-tetradec-9-en-1-yl acetate, I+(7E,9Z)-dodeca-7,9-dien-1-yl acetate, I+(9Z,11E)-tetradeca-9,11-dien-1-yl acetate, I+(9Z,12E)-tetradeca-9,12-dien-1-yl acetate, I+14-methyloctadec-1-ene, I+4-methylnonan-5-ol with 4-methylnonan-5-one, I+alpha-multistriatin, I+brevicomin, I+codlelure, I+codlemone, I+cuelure, I+disparlure, I+dodec-8-en-1-yl acetate, I+dodec-9-en-1-yl acetate, I+dodeca-8, I+10-dien-1-yl acetate, I+dominicalure, I+ethyl 4-methyloctanoate, I+eugenol, I+frontalin, I+gossyplure, I+grandlure, I+grandlure I, I+grandlure II, I+grandlure III, I+grandlure IV, I+hexalure, I+ipsdienol, I+ipsenol, I+japonilure, I+lineatin, I+litlure, I+looplure, I+medlure, I+megatomoic acid, I+methyl eugenol, I+muscalure, I+octadeca-2,13-dien-1-yl acetate, I+octadeca-3,13-dien-1-yl acetate, I+orfralure, I+oryctalure, I+ostramone, I+siglure, I+sordidin, I+sulcatol, I+tetradec-11-en-1-yl acetate, I+trimedlure, I+trimedlure A, I+trimedlure $B_1$, I+trimedlure $B_2$, I+trimedlure C and I+trunc-call.

Compositions comprising an insect repellent include I+2-(octylthio)ethanol, I+butopyronoxyl, I+butoxy(polypropylene glycol), I+dibutyl adipate, I+dibutyl phthalate, I+dibutyl succinate, I+diethyltoluamide, I+dimethyl carbate, I+dimethyl phthalate, I+ethyl hexanediol, I+hexamide, I+methoquin-butyl, I+methylneodecanamide, I+oxamate and I+picaridin.

Compositions comprising an insecticide include I+1-dichloro-1-nitroethane, I+1,1-dichloro-2,2-bis(4-ethylphenyl) ethane, I+, I+1,2-dichloropropane, I+1,2-dichloropropane with 1,3-dichloropropene, I+1-bromo-2-chloroethane, I+2,2,2-trichloro-1-(3,4-dichlorophenyl)ethyl acetate, I+2,2-dichlorovinyl 2-ethylsulfinylethyl methyl phosphate, I+2-(1,3-dithiolan-2-yl)phenyl dimethylcarbamate, I+2-(2-butoxyethoxy)ethyl thiocyanate, I+2-(4,5-dimethyl-1,3-dioxolan-2-yl)phenyl methylcarbamate, I+2-(4-chloro-3,5-xylyloxy)ethanol, I+2-chlorovinyl diethyl phosphate, I+2-imidazolidone, I+2-isovalerylindan-1,3-dione, I+2-methyl (prop-2-ynyl)aminophenyl methylcarbamate, I+2-thiocyanatoethyl laurate, I+3-bromo-1-chloroprop-1-ene, I+3-methyl-1-phenylpyrazol-5-yl dimethylcarbamate, I+4-methyl(prop-2-ynyl)amino-3,5-xylyl methylcarbamate, I+5,5-dimethyl-3-oxocyclohex-1-enyl dimethylcarbamate, I+abamectin, I+acephate, I+acetamiprid, I+acethion, I+acetoprole, I+acrinathrin, I+acrylonitrile, I+alanycarb, I+aldicarb, I+aldoxycarb, I+aldrin, I+allethrin, I+allosamidin, I+allyxycarb, I+alpha-cypermethrin, I+alpha-ecdysone, I+aluminium phosphide, I+amidithion, I+amidothioate, I+aminocarb, I+amiton, I+amiton hydrogen oxalate, I+amitraz, I+anabasine, I+athidathion, I+AVI 382, I+AZ 60541, I+azadirachtin, I+azamethiphos, I+azinphos-ethyl, I+azinphos-methyl, I+azothoate, I+*Bacillus thuringiensis* delta endotoxins, I+barium hexafluorosilicate, I+barium polysulfide, I+barthrin, I+Bayer 22/190, I+Bayer 22408, I+bendiocarb, I+benfuracarb, I+bensultap, I+beta-cyfluthrin, I+beta-cypermethrin, I+bifenthrin, I+bioallethrin, I+bioallethrin S-cyclopentenyl isomer, I+bioethanomethrin, I+biopermethrin, I+bioresmethrin, I+bis(2-chloroethyl) ether, I+bistrifluron, I+borax, I+brofenvalerate, I+bromfenvinfos, I+bromocyclen, I+bromo-DDT, I+bromophos, I+bromophos-ethyl, I+bufencarb, I+buprofezin, I+butacarb, I+butathiofos, I+butocarboxim, I+butonate, I+butoxycarboxim, I+butylpyridaben, I+cadusafos, I+calcium arsenate, I+calcium cyanide, I+calcium polysulfide, I+camphechlor, I+carbanolate, I+carbaryl, I+carbofuran, I+carbon disulfide, I+carbon tetrachloride, I+carbophenothion, I+carbosulfan, I+cartap, I+cartap hydrochloride, I+cevadine, I+chlorbicyclen, I+chlordane, I+chlordecone, I+chlordimeform, I+chlordimeform hydrochloride, I+chlorethoxyfos, I+chlorfenapyr, I+chlorfenvinphos, I+chlorfluazuron, I+chlormephos, I+chloroform, I+chloropicrin, I+chlorphoxim, I+chlorprazophos, I+chlorpyrifos, I+chlorpyrifos-methyl, I+chlorthiophos, I+chromafenozide, I+cinerin I, I+cinerin II, I+cinerins, I+cis-resmethrin, I+cismethrin, I+clocythrin, I+cloethocarb, I+closantel, I+clothianidin, I+copper acetoarsenite, I+copper arsenate, I+copper oleate, I+coumaphos, I+coumithoate, I+crotamiton, I+crotoxyphos, I+crufomate, I+cryolite, I+CS 708, I+cyanofenphos, I+cyanophos, I+cyanthoate, I+cyclethrin, I+cycloprothrin, I+cyfluthrin, I+cyhalothrin, I+cypermethrin, I+cyphenothrin, I+cyromazine, I+cythioate, I+d-limonene, I+d-tetramethrin, I+DAEP, I+dazomet, I+DDT, I+decarbofuran, I+deltamethrin, I+demephion, I+demephion-O, I+demephion-S, I+demeton, I+demeton-methyl, I+demeton-O, I+demeton-O-methyl, I+demeton-S, I+demeton-S-methyl, I+demeton-S-methylsulphon, I+diafenthiuron, I+dialifos, I+diamidafos, I+diazinon, I+dicapthon, I+dichlofenthion, I+dichlorvos, I+dicliphos, I+dicresyl, I+dicrotophos, I+dicyclanil, I+dieldrin, I+diethyl 5-methylpyrazol-3-yl phosphate, I+diflubenzuron, I+dilor, I+dimefluthrin, I+dimefox, I+dimetan, I+dimethoate, I+dimethrin, I+dimethylvinphos, I+dimetilan, I+dinex, I+dinex-diclexine, I+dinoprop, I+dinosam, I+dinoseb, I+dinotefuran, I+diofenolan, I+dioxabenzofos, I+dioxacarb, I+dioxathion, I+disulfoton, I+dithicrofos, I+DNOC, I+doramectin, I+DSP, I+ecdysterone, I+EI 1642, I+emamectin, I+emamectin benzoate, I+EMPC, I+empenthrin, I+endosulfan, I+endothion, I+endrin, I+EPBP, I+EPN, I+epofenonane, I+eprinomectin, I+esfenvalerate, I+etaphos, I+ethiofencarb, I+ethion, I+ethiprole, I+ethoate-methyl, I+ethoprophos, I+ethyl formate, I+ethyl-DDD, I+ethylene dibromide, I+ethylene dichloride, I+ethylene oxide, I+etofenprox, I+etrimfos, I+EXD, I+famphur, I+fenamiphos, I+fenazaflor, I+fenchlorphos, I+fenethacarb, I+fenfluthrin, I+fenitrothion, I+fenobucarb, I+fenoxacrim, I+fenoxycarb, I+fenpirithrin, I+fenpropathrin, I+fenpyrad, I+fensulfothion, I+fenthion, I+fenthion-ethyl, I+fenvalerate, I+fipronil, I+flonicamid, I+flubendiamide, I+flucofuron, I+flucycloxuron, I+flucythrinate, I+fluenetil, I+flufenerim, I+flufenoxuron, I+flufenprox, I+flumethrin, I+fluvalinate, I+FMC 1137, I+fonofos, I+formetanate, I+formetanate hydrochloride, I+formothion, I+formparanate, I+fosmethilan, I+fospirate, I+fosthiazate, I+fosthietan, I+furathiocarb, I+furethrin, I+gamma-cyhalothrin, I+gamma-HCH, I+guazatine, I+guazatine acetates, I+GY-81, I+halfenprox, I+halofenozide, I+HCH, I+HEOD, I+heptachlor, I+heptenophos, I+heterophos, I+hexaflumuron, I+HHDN, I+hydramethylnon, I+hydrogen cyanide, I+hydroprene, I+hyquincarb, I+imidacloprid, I+imiprothrin, I+indoxacarb, I+iodomethane, I+IPSP, I+isazofos, I+isobenzan, I+isocarbophos, I+isodrin, I+isofenphos, I+isolane, I+isoprocarb, I+isopropyl O-(methoxyaminothiophosphoryl)salicylate, I+isoprothiolane, I+isothioate, I+isoxathion, I+ivermectin, I+jasmolin I, I+jasmolin II, I+jodfenphos, I+juvenile hormone I, I+juvenile hormone II, I+juvenile hormone III, I+kelevan, I+kinoprene, I+lambda-cyhalothrin, I+lead arsenate, I+lepimectin, I+leptophos, I+lindane, I+lirimfos, I+lufenuron, I+lythidathion, I+m-cumenyl methylcarbamate, I+magnesium phosphide, I+malathion, I+malonoben, I+mazidox, I+mecarbam, I+mecarphon, I+menazon, I+mephosfolan, I+mercurous chloride, I+mesulfenfos, I+metaflumizone, I+metam, I+metam-potassium, I+metam-sodium, I+methacrifos, I+methamidophos, I+methanesulfonyl fluoride, I+methidathion, I+methiocarb, I+methocrotophos, I+methomyl, I+methoprene, I+methoquin-butyl, I+methothrin, I+methoxychlor, I+methoxyfenozide, I+methoxyfenozide, I+methyl bromide, I+methyl isothiocyanate, I+methylchloroform, I+methylene chloride, I+metofluthrin, I+metolcarb, I+metoxadiazone, I+mevinphos, I+mexacarbate, I+milbemectin, I+milbemycin oxime, I+mipafox, I+mirex, I+monocrotophos, I+morphothion, I+moxidectin, I+naftalofos, I+naled, I+naphthalene, I+NC-170, I+NC-184, I+nicotine, I+nicotine sulfate, I+nifluridide, I+nitenpyram, I+nithiazine, I+nitrilacarb, I+nitrilacarb 1:1 zinc chloride complex, I+NNI-0101, I+NNI-0250, I+nornicotine, I+novaluron, I+noviflumuron, I+O-5-dichloro-4-iodophenyl O-ethyl ethylphosphonothioate, I+O,O-diethyl O-4-methyl-2-oxo-2H-chromen-7-yl phosphorothioate, I+O,O-diethyl O-6-methyl-2-propylpyrimidin-4-yl phosphorothioate, I+O,O,O',O'-tetrapropyl dithiopyrophosphate, I+oleic acid, I+omethoate, I+oxamyl, I+oxydemeton-methyl, I+oxydeprofos, I+oxydisulfoton, I+pp'-DDT, I+para-dichlorobenzene, I+parathion, I+parathion-methyl, I+penfluron, I+pentachlorophenol, I+pentachlorophenyl laurate, I+permethrin, I+petroleum oils, I+PH 60-38, I+phenkapton, I+phenothrin, I+phenthoate, I+phorate+TX, I+phosalone, I+phosfolan, I+phosmet, I+phosnichlor, I+phosphamidon, I+phosphine, I+phoxim, I+phoxim-methyl, I+pirimetaphos, I+pirimicarb, I+pirimiphos-ethyl, I+pirimiphos-methyl, I+polychlorodicyclopentadiene isomers, I+polychloroterpenes, I+potassium arsenite, I+potassium thiocyanate, I+prallethrin, I+precocene I, I+precocene II, I+precocene III, I+primidophos, I+profenofos, I+profluthrin, I+promacyl, I+promecarb, I+propaphos, I+propetamphos, I+propoxur, I+prothidathion, I+prothiofos, I+prothoate, I+protrifenbute, I+pymetrozine, I+pyraclofos, I+pyrazophos, I+pyresmethrin, I+pyrethrin I, I+pyrethrin II, I+pyrethrins, I+pyridaben, I+pyridalyl, I+pyridaphenthion, I+pyrimidifen, I+pyrimitate, I+pyriproxyfen, I+quassia, I+quinalphos, I+quinalphos-methyl, I+quinothion, I+quintiofos, I+R-1492, I+rafoxanide, I+resmethrin, I+rotenone, I+RU 15525, I+RU 25475, I+ryania, I+ryanodine, I+sabadilla, I+schradan, I+sebufos, I+selamectin, I+SI-0009, I+SI-0205, I+SI-0404, I+SI-0405, I+silafluofen, I+SN 72129, I+sodium arsenite, I+sodium cyanide, I+sodium fluoride, I+sodium hexafluorosilicate, I+sodium pentachlorophenoxide, I+sodium selenate, I+sodium thiocyanate, I+sophamide, I+spinosad, I+spiromesifen, I+spirotetrmat, I+sulcofuron, I+sulcofuron-sodium, I+sulfluramid, I+sulfotep, I+sulfuryl fluoride, I+sulprofos, I+tar oils, I+tau-fluvalinate, I+tazimcarb, I+TDE, I+tebufenozide, I+tebufenpyrad, I+tebupirimfos, I+teflubenzuron, I+tefluthrin, I+temephos, I+TEPP, I+terallethrin, I+terbam, I+terbufos, I+tetrachloroethane, I+tetrachlorvinphos, I+tetramethrin, I+theta-cypermethrin, I+thiacloprid, I+thiafenox, I+thiamethoxam, I+thicrofos, I+thiocarboxime, I+thiocyclam, I+thiocyclam hydrogen oxalate, I+thiodicarb, I+thiofanox, I+thiometon, I+thionazin, I+thiosultap, I+thiosultap-sodium, I+thuringiensin, I+tolfenpyrad, I+tralomethrin, I+transfluthrin, I+transpermethrin, I+triamiphos, I+triazamate, I+triazophos, I+triazuron, I+trichlorfon, I+trichlormetaphos-3, I+trichloronat, I+trifenofos, I+triflumuron, I+trimethacarb, I+triprene, I+vamidothion, I+vaniliprole, I+veratridine, I+veratrine, I+XMC, I+xylylcarb, I+YI-5302, I+zeta-cypermethrin, I+zetamethrin, I+zinc phosphide, I+zolaprofos and ZXI 8901, I+cyantraniliprole, I+chlorantraniliprole, I+cyenopyrafen, I+cyflumetofen, I+pyrifluquinazon, I+spinetoram, I+spirotetramat, I+sulfoxaflor, I+flufiprole, I+meperfluthrin, I+tetramethylfluthrin, I+triflumezopyrim.

Compositions comprising a molluscicide include I+bis (tributyltin) oxide, I+bromoacetamide, I+calcium arsenate, I+cloethocarb, I+copper acetoarsenite, I+copper sulfate, I+fentin, I+ferric phosphate, I+metaldehyde, I+methiocarb, I+niclosamide, I+niclosamide-olamine, I+pentachlorophenol, I+sodium pentachlorophenoxide, I+tazimcarb, I+thiodicarb, I+tributyltin oxide, I+trifenmorph, I+trimethacarb, I+triphenyltin acetate and triphenyltin hydroxide, I+pyriprole.

Compositions comprising a nematicide include I+AKD-3088, I+1,2-dibromo-3-chloropropane, I+1,2-dichloropropane, I+1,2-dichloropropane with 1,3-dichloropropene, I+1,3-dichloropropene, I+3,4-dichlorotetrahydrothiophene 1,1-dioxide, I+3-(4-chlorophenyl)-5-methylrhodanine, I+5-methyl-6-thioxo-1,3,5-thiadiazinan-3-ylacetic acid, I+6-isopentenylaminopurine, I+abamectin, I+acetoprole, I+alanycarb, I+aldicarb, I+aldoxycarb, I+AZ 60541, I+benclothiaz, I+benomyl, I+butylpyridaben, I+cadusafos, I+carbofuran, I+carbon disulfide, I+carbosulfan, I+chloropicrin, I+chlorpyrifos, I+cloethocarb, I+cytokinins, I+dazomet, I+DBCP, I+DCIP, I+diamidafos, I+dichlofenthion, I+dicliphos, I+dimethoate, I+doramectin, I+emamectin, I+emamectin benzoate, I+eprinomectin, I+ethoprophos, I+ethylene dibromide, I+fenamiphos, I+fenpyrad, I+fensulfothion, I+fosthiazate, I+fosthietan, I+furfural, I+GY-81, I+heterophos, I+iodomethane, I+isamidofos, I+isazofos, I+ivermectin, I+kinetin, I+mecarphon, I+metam, I+metam-potassium, I+metam-sodium, I+methyl bromide, I+methyl isothiocyanate, I+milbemycin oxime, I+moxidectin, I+*Myrothecium verrucaria* composition, I+NC-184, I+oxamyl, I+phorate, I+phosphamidon, I+phosphocarb, I+sebufos, I+selamectin, I+spinosad, I+terbam, I+terbufos, I+tetrachlorothiophene, I+thiafenox, I+thionazin, I+triazophos, I+triazuron, I+xylenols, I+YI-5302 and zeatin, I+fluensulfone.

Compositions comprising a synergist include I+2-(2-butoxyethoxy)ethyl piperonylate, I+5-(1,3-benzodioxol-5-yl)-3-hexylcyclohex-2-enone, I+farnesol with nerolidol, I+MB-599, I+MGK 264, I+piperonyl butoxide, I+piprotal, I+propyl isomer, I+S421, I+sesamex, I+sesasmolin and I+sulfoxide.

Compositions comprising an animal repellent include I+anthraquinone, I+chloralose, I+copper naphthenate, I+copper oxychloride, I+diazinon, I+dicyclopentadiene, I+guazatine, I+guazatine acetates, I+methiocarb, I+pyridin-4-amine, I+thiram, I+trimethacarb, I+zinc naphthenate and I+ziram.

Further compositions include I+Brofluthrinate, I+Cycloxaprid, I+Diflovidazine, I+Flometoquin, I+Fluhexafon, I+Guadipyr, I+*Plutella xylostella* Granulosis virus, I+*Cydia pomonella* Granulosis virus, I+Harpin, I+Imicyafos, I+*Heliothis virescens* Nucleopolyhedrovirus, I+*Heliothis punctigera* Nucleopolyhedrovirus, I+*Helicoverpa armigera* Nucleopolyhedrovirus, I+*Helicoverpa zea* Nucleopolyhedrovirus, I+*Spodoptera frugiperda* Nucleopolyhedrovirus, I+*Plutella xylostella* Nucleopolyhedrovirus, I+*Pasteuria nishizawae*, I+p-cymene, I+Pyflubumide, I+Pyrafluprole, I+pyrethrum, I+QRD 420, I+QRD 452, I+QRD 460, I+Terpenoid blends, I+Terpenoids, I+Tetraniliprole, and I+α-terpinene.

Composition also include mixtures of the polymorph or polymorphs of the invention and an active substance referenced by a code, such as I+code AE 1887196 (BSC-BX60309), I+code NNI-0745 GR, I+code IKI-3106, I+code JT-L001, I+code ZNQ-08056, I+code IPPA152201, I+code HNPC-A9908 (CAS: [660411-21-2]), I+code HNPC-A2005 (CAS: [860028-12-2]), I+code JS118, I+code ZJ0967, I+code ZJ2242, I+code JS7119 (CAS: [929545-74-4]), I+code SN-1172, I+code HNPC-A9835, I+code HNPC-A9955, I+code HNPC-A3061, I+code Chuanhua 89-1, I+code IPP-10, I+code ZJ3265, I+code JS9117, I+code SYP-9080, I+code ZJ3757, I+code ZJ4042, I+code ZJ4014, I+code ITM-121, I+code DPX-RAB55 (DKI-2301), I+code Me5382, I+code NC-515, I+code NA-89, I+code MIE-1209, I+code MCI-8007, I+code BCS-CL73507, I+code S-1871, I+code DPX-RDS63, and I+code AKD-1193.

Whilst compositions comprising the polymorph or polymorphs of the invention and another insecticide etc. are explicitly disclosed above, the skilled man will appreciate that the invention extends to three-way, and further multiple combinations comprising the above two-way mixtures.

The weight ratio of the polymorph or polymorphs of the invention and another insecticide is generally between 1000:1 and 1:100, more preferably between 500:1 and 1:100, for example between 250:1 and 1:66, between 125:1 and 1:33, between 100:1 and 1:25, between 66:1 and 1:10, between 33:1 and 1:5 and between 8:1 and 1:3.

The polymorphs of the invention are also useful in the field of animal health, e.g. they may be used against parasitic invertebrate pests, more preferably against parasitic invertebrate pests in or on an animal. Examples of pests include nematodes, trematodes, cestodes, flies, mites, tricks, lice, fleas, true bugs and maggots. The animal may be a non-human animal, e.g. an animal associated with agriculture, e.g. a cow, a pig, a sheep, a goat, a horse, or a donkey, or a companion animal, e.g. a dog or a cat.

In a further aspect the invention provides a polymorph of the invention for use in a method of therapeutic treatment.

In a further aspect the invention relates to a method of controlling parasitic invertebrate pests in or on an animal comprising administering a pesticidally effective amount of a polymorph of the invention. The administration may be for example oral administration, parenteral administration or external administration, e.g. to the surface of the animal body. In a further aspect the invention relates to a polymorph of the invention for controlling parasitic invertebrate pests in or on an animal. In a further aspect the invention relates to use of a polymorph of the invention in the manufacture of a medicament for controlling parasitic invertebrate pests in or on an animal.

In a further aspect, the invention relates to a method of controlling parasitic invertebrate pests comprising administering a pesticidally effective amount of a polymorph of the invention to the environment in which an animal resides.

In a further aspect the invention relates to a method of protecting an animal from a parasitic invertebrate pest comprising administering to the animal a pesticidally effective amount of a polymorph of the invention. In a further aspect the invention relates to a polymorph of the invention for use in protecting an animal from a parasitic invertebrate pest. In a further aspect the invention relates to use of a polymorph of the invention in the manufacture of a medicament for protecting an animal from a parasitic invertebrate pest.

In a further aspect the invention provides a method of treating an animal suffering from a parasitic invertebrate pest comprising administering to the animal a pesticidally effective amount of a polymorph of the invention. In a further aspect the invention relates to a polymorph of the invention for use in treating an animal suffering from a parasitic invertebrate pest. In a further aspect the invention relates to use of a polymorph of the invention in the manufacture of a medicament for treating an animal suffering from a parasitic invertebrate pest.

In a further aspect, the invention provides a pharmaceutical composition comprising a polymorph of the invention and a pharmaceutically suitable excipient.

The polymorph of the invention may be used alone or in combination with one or more other biologically active ingredients.

In one aspect the invention provides a combination product comprising a pesticidally effective amount of a component A and a pesticidally effective amount of component B wherein component A is a polymorph of the invention and component B is a compound as described below.

The polymorph of the invention may be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The polymorphs of the invention may be used in combination with derivatives and analogues of the paraherquamide/marcfortine class of anthelmintic agents, as well as the antiparasitic oxazolines such as those disclosed in U.S. Pat. Nos. 5,478,855, 4,639,771 and DE-19520936.

The polymorphs of the invention may be used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

The polymorphs of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The polymorphs of the invention may be used in combination with terpene alkaloids, for example those described in International Patent Application Publication Numbers WO95/19363 or WO04/72086, particularly the compounds disclosed therein.

Other examples of such biologically active compounds that the polymorphs of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1 R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halo fenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Fungicides: acibenzolar, aldimorph, ampropylfos, andoprim, azaconazole, azoxystrobin, benalaxyl, benomyl, bialaphos, blasticidin-S, Bordeaux mixture, bromuconazole, bupirimate, carpropamid, captafol, captan, carbendazim, chlorfenazole, chloroneb, chloropicrin, chlorothalonil, chlozolinate, copper oxychloride, copper salts, cyflufenamid, cymoxanil, cyproconazole, cyprodinil, cyprofuram, RH-7281, diclocymet, diclobutrazole, diclomezine, dicloran, difenoconazole, RP-407213, dimethomorph, domoxystrobin, diniconazole, diniconazole-M, dodine, edifenphos, epoxiconazole, famoxadone, fenamidone, fenarimol, fenbuconazole, fencaramid, fenpiclonil, fenpropidin, fenpropimorph, fentin acetate, fluazinam, fludioxonil, flumetover, flumorf/flumorlin, fentin hydroxide, fluoxastrobin, fluquinconazole, flusilazole, flutolanil, flutriafol, folpet, fosetyl-aluminium, furalaxyl, furametapyr, hexaconazole, ipconazole, iprobenfos, iprodione, isoprothiolane, kasugamycin, krsoxim-methyl, mancozeb, maneb, mefenoxam, mepronil, metalaxyl, metconazole, metominostrobin/fenominostrobin, metrafenone, myclobutanil, neo-asozin, nicobifen, orysastrobin, oxadixyl, penconazole, pencycuron, probenazole, prochloraz, propamocarb, propioconazole, proquinazid, prothioconazole, pyrifenox, pyraclostrobin, pyrimethanil, pyroquilon, quinoxyfen, spiroxamine, sulfur, tebuconazole, tetrconazole, thiabendazole, thifluzamide, thiophanate-methyl, thiram, tiadinil, triadimefon, triadimenol, tricyclazole, trifloxystrobin, triticonazole, validamycin, vinclozin.

Biological agents: *Bacillus thuringiensis* ssp *aizawai, kurstaki, Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

When used in combination with other active ingredients, the polymorphs of the invention are preferably used in combination with imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene (including S-methoprene), clorsulon, pyrantel, amitraz, triclabendazole, avermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone or tebufenozide; more preferably, enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon, pyrantel, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, lufenuron or ecdysone; even more preferably, enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon or pyrantel.

Of particular note is a combination where the additional active ingredient has a different site of action from the polymorph of the invention. In certain instances, a combination with at least one other parasitic invertebrate pest control active ingredient having a similar spectrum of control but a different site of action will be particularly advantageous for resistance management. Thus, a combination product of the invention may comprise a pesticidally effective amount of a polymorph of the invention and pesticidally effective amount of at least one additional parasitic invertebrate pest control active ingredient having a similar spectrum of control but a different site of action.

One skilled in the art recognizes that because in the environment and under physiological conditions salts of chemical compounds are in equilibrium with their corresponding non salt forms, salts share the biological utility of the non salt forms.

Thus a wide variety of salts of polymorphs of the invention (and active ingredients used in combination with the active ingredients of the invention) may be useful for control of invertebrate pests and animal parasites. Salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The polymorphs of the invention also include N-oxides. Accordingly, the invention comprises combinations of polymorphs of the invention including N-oxides and salts thereof and an additional active ingredient including N-oxides and salts thereof.

The compositions for use in animal health may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in McCutcheon's Volume 2: Functional Materials, annual International and North American editions published by McCutcheon's Division, The Manufacturing Confectioner Publishing Co.; and PCT Publication WO 03/024222.

The polymorphs of the invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of the combination products. Compositions with spray oils, spray oil concentrations, spreader stickers, adjuvants, other solvents, and synergists such as piperonyl butoxide often enhance compound efficacy. Such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a pesticidally effective amount of a compound of the invention and a carrier. One embodiment of such a spray composition comprises a pesticidally effective amount of a compound of the invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one parasitic invertebrate pest selected from the group consisting of mosquitoes, black flies, stable flies, deer flies, horse flies, wasps, yellow jackets, hornets, ticks, spiders, ants, gnats, and the like, including individually or in combinations.

The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. The polymorphs of the invention may be particularly suitable for combating external parasitic pests. The polymorphs of the invention may be suitable for systemic and/or non-systemic control of infestation or infection by parasites on animals.

The polymorphs of the invention may be suitable for combating parasitic invertebrate pests that infest animal subjects including those in the wild, livestock and agricultural working animals. Livestock is the term used to refer (singularly or plurally) to a domesticated animal intentionally reared in an agricultural setting to make produce such as food or fiber, or for its labor; examples of livestock include cattle, sheep, goats, horses, pigs, donkeys, camels, buffalo, rabbits, hens, turkeys, ducks and geese (e.g., raised for meat, milk, butter, eggs, fur, leather, feathers and/or wool). By combating parasites, fatalities and performance reduction (in terms of meat, milk, wool, skins, eggs, etc.) are reduced, so that applying the polymorphs of the invention allows more economic and simple husbandry of animals.

The polymorphs of the invention may be suitable for combating parasitic invertebrate pests that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Birds treated or protected by the polymorphs of the invention can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws and parrots raised for the pet or collector market, among others.

For purposes of the present invention, the term "fish" is understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of parasitic invertebrate pests controlled by administering a pesticidally effective amount of the polymorphs of the invention to an animal to be protected include ectoparasites (arthropods, acarines, etc.) and endoparasites (helminths, e.g., nematodes, trematodes, cestodes, acanthocephalans, etc.).

The disease or group of diseases described generally as helminthiasis is due to infection of an animal host with parasitic worms known as helminths. The term 'helminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the helminths, the group of worms described as nematodes causes widespread and at times serious infection in various species of animals.

Nematodes that are contemplated to be treated by the polymorphs of the invention include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria* and *Wuchereria*.

Of the above, the most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Certain of these, such as *Nematodirus, Cooperia* and *Oesophagostomum* attack primarily the intestinal tract while others, such as *Haemonchus* and *Ostertagia*, are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the invention and by the inventive methods include, without limitation, the following genera: *Alaria, Fasciola, Nanophyetus, Opisthorchis, Paragonimus* and *Schistosoma*.

Cestodes that are contemplated to be treated by the invention and by the inventive methods include, without limitation, the following genera: *Diphyllobothrium, Diplydium, Spirometra* and *Taenia*.

The most common genera of parasites of the gastrointestinal tract of humans are *Ancylostoma, Necator, Ascaris, Strongy hides, Trichinella, Capillaria, Trichuris* and *Enterobius*. Other medically important genera of parasites which are found in the blood or other tissues and organs outside the gastrointestinal tract are the filarial worms such as *Wuchereria, Brugia, Onchocerca* and *Loa*, as well as *Dracunculus* and extra intestinal stages of the intestinal worms *Strongyloides* and *Trichinella*.

Numerous other helminth genera and species are known to the art, and are also contemplated to be treated by the polymorphs of the invention. These are enumerated in great detail in Textbook of Veterinary Clinical Parasitology, Volume 1, Helminths, E. J. L. Soulsby, F. A. Davis Co., Philadelphia, Pa.; Helminths, Arthropods and Protozoa, (6th Edition of Monnig's Veterinary Helminthology and Entomology), E. J. L. Soulsby, Williams and Wilkins Co., Baltimore, Md.

The polymorphs of the invention may be effective against a number of animal ectoparasites (e.g., arthropod ectoparasites of mammals and birds).

Insect and acarine pests include, e.g., biting insects such as flies and mosquitoes, mites, ticks, lice, fleas, true bugs, parasitic maggots, and the like.

Adult flies include, e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, and the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax*, the cattle grub or *Hypoderma* spp., the fleeceworm and the Gastrophilus of horses. Mosquitoes include, for example, *Culex* spp., *Anopheles* spp. and *Aedes* spp.

Mites include *Mesostigmalphatalpha* spp. e.g., mesostigmatids such as the chicken mite, *Dermalphanyssus galphallinalphae*; itch or scab mites such as *Sarcoptidae* spp. for example, *Salpharcoptes scalphabiei*; mange mites such as *Psoroptidae* spp. including *Chorioptes bovis* and *Psoroptes ovis*; chiggers e.g., *Trombiculidae* spp. for example the North American chigger, *Trombiculalpha alphalfreddugesi*.

Ticks include, e.g., soft-bodied ticks including *Argasidae* spp. for example *Argalphas* spp. and *Ornithodoros* spp.; hard-bodied ticks including *Ixodidae* spp., for example *Rhipicephalphalus sanguineus, Dermacentor variabilis, Dermacentor andersoni, Amblyomma americanum, Ixodes scapularis* and other *Rhipicephalus* spp. (including the former *Boophilus* genera).

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides fells*); *Xenopsylla* spp. such as oriental rat flea (*Xenopsylla cheopis*); and *Pulex* spp. such as human flea (*Pulex irritans*).

True bugs include, e.g., *Cimicidae* or e.g., the common bed bug (*Cimex lectularius*); *Triatominae* spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other parasitic invertebrate pests are known to the art, and are also contemplated to be treated by the polymorphs of the invention. These are enumerated in great detail in Medical and Veterinary Entomology, D. S. Kettle, John Wiley AND Sons, New York and Toronto; Control of Arthropod Pests of Livestock: A Review of Technology, R. O. Drummand, J. E. George, and S. E. Kunz, CRC Press, Boca Raton, Fla.

The polymorphs of the invention may also be effective against ectoparasites including: flies such as *Haematobia* (*Lyperosia*) *irritans* (horn fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus intestinalis, Gastrophilus haemorrhoidalis* and *Gastrophilus nasalis*; lice such as *Bovicola* (Damalinia) *bovis, Bovicola equi, Haematopinus asini, Felicola subrostratus, Heterodoxus spiniger, Lignonathus setosus* and *Trichodectes canis*; keds such as *Melophagus ovinus*; and mites such as *Psoroptes* spp., *Sarcoptes scabei, Chorioptes bovis, Demodex equi, Cheyletiella* spp., *Notoedres cati, Trombicula* spp. and *Otodectes cyanotis* (ear mites).

Treatments of the invention are by conventional means such as by enteral administration in the form of, for example, tablets, capsules, drinks, drenching preparations, granulates, pastes, boli, feed-through procedures, or suppositories; or by parenteral administration, such as, for example, by injection (including intramuscular, subcutaneous, intravenous, intraperitoneal) or implants; or by nasal administration.

When polymorphs of the invention are applied in combination with an additional biologically active ingredient, they may be administered separately e.g. as separate compositions. In this case, the biologically active ingredients may be administered simultaneously or sequentially. Alternatively, the biologically active ingredients may be components of one composition.

The polymorphs of the invention may be administered in a controlled release form, for example in subcutaneous or orally adminstered slow release formulations.

Typically a parasiticidal composition according to the present invention comprises a polymorph of the invention, optionally in combination with an additional biologically active ingredient, or N-oxides or salts thereof, with one or more pharmaceutically or veterinarily acceptable carriers comprising excipients and auxiliaries selected with regard to the intended route of administration (e.g., oral or parenteral administration such as injection) and in accordance with standard practice. In addition, a suitable carrier is selected on the basis of compatibility with the one or more active ingredients in the composition, including such considerations as stability relative to pH and moisture content. Therefore of note are polymorph of the invention for protecting an animal from an invertebrate parasitic pest comprising a parasitically effective amount of a polymorph of the invention, optionally in combination with an additional biologically active ingredient and at least one carrier.

For parenteral administration including intravenous, intramuscular and subcutaneous injection, the polymorphs of the invention can be formulated in suspension, solution or emulsion in oily or aqueous vehicles, and may contain adjuncts such as suspending, stabilizing and/or dispersing agents.

The polymorphs of the invention may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes.

Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the polymorphs of the invention may also be formulated as a depot preparation. Such long acting formulations may be administered by implantation (for example, subcutaneously or intramuscularly) or by intramuscular or subcutaneous injection.

The polymorphs of the invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the polymorphs of the invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount.

Capsules and cartridges of, for example, gelatin for use in an inhaler or insufflator may be formulated containing a powder mix of the compound and a suitable powder base such as lactose or starch.

The polymorphs of the invention may have favourable pharmacokinetic and pharmacodynamic properties providing systemic availability from oral administration and ingestion. Therefore after ingestion by the animal to be protected, parasiticidally effective concentrations of a polymorph of the invention in the bloodstream may protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a polymorph of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, the polymorph of the invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

In one embodiment a composition of the present invention is formulated into a chewable and/or edible product (e.g., a chewable treat or edible tablet). Such a product would ideally have a taste, texture and/or aroma favored by the animal to be protected so as to facilitate oral administration of the compounds of the invention.

If the parasiticidal compositions are in the form of feed concentrates, the carrier is typically selected from high-performance feed, feed cereals or protein concentrates. Such feed concentrate-containing compositions can, in addition to the parasiticidal active ingredients, comprise additives promoting animal health or growth, improving quality of meat from animals for slaughter or otherwise useful to animal husbandry. These additives can include, for example, vitamins, antibiotics, chemotherapeutics, bacteriostats, fungistats, coccidiostats and hormones.

The polymorph of the invention may also be formulated in rectal compositions such as suppositories or retention enemas, using, e.g., conventional suppository bases such as cocoa butter or other glycerides.

The formulations for the method of this invention may include an antioxidant, such as BHT (butylated hydroxytoluene). The antioxidant is generally present in amounts of at 0.1-5 percent (wt/vol). Some of the formulations require a solubilizer, such as oleic acid, to dissolve the active agent, particularly if spinosad is included. Common spreading agents used in these pour-on formulations include isopropyl myristate, isopropyl palmitate, caprylic/capric acid esters of saturated $C_{12}$-$C_{18}$ fatty alcohols, oleic acid, oleyl ester, ethyl oleate, triglycerides, silicone oils and dipropylene glycol methyl ether. The pour-on formulations for the method of this invention are prepared according to known techniques. Where the pour-on is a solution, the parasiticide/insecticide is mixed with the carrier or vehicle, using heat and stirring if required. Auxiliary or additional ingredients can be added to the mixture of active agent and carrier, or they can be mixed with the active agent prior to the addition of the carrier. Pour-on formulations in the form of emulsions or suspensions are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

The rate of application required for effective parasitic invertebrate pest control (e.g. "pesticidally effective amount") will depend on such factors as the species of parasitic invertebrate pest to be controlled, the pest's life cycle, life stage, its size, location, time of year, host crop or animal, feeding behavior, mating behavior, ambient moisture, temperature, and the like. One skilled in the art can easily determine the pesticidally effective amount necessary for the desired level of parasitic invertebrate pest control.

In general for veterinary use, the polymorphs of the invention are administered in a pesticidally effective amount to an animal, particularly a homeothermic animal, to be protected from parasitic invertebrate pests.

A pesticidally effective amount is the amount of active ingredient needed to achieve an observable effect diminishing the occurrence or activity of the target parasitic invertebrate pest. One skilled in the art will appreciate that the pesticidally effective dose can vary for the various compounds and compositions useful for the method of the present invention, the desired pesticidal effect and duration, the target parasitic invertebrate pest species, the animal to be protected, the mode of application and the like, and the amount needed to achieve a particular result can be determined through simple experimentation.

For oral or parenteral administration to animals, a dose of the compositions of the present invention administered at suitable intervals typically ranges from about 0.01 mg/kg to about 100 mg/kg, and preferably from about 0.01 mg/kg to about 30 mg/kg of animal body weight.

Suitable intervals for the administration of the compositions of the present invention to animals range from about daily to about yearly. Of note are administration intervals ranging from about weekly to about once every 6 months. Of particular note are monthly adminstration intervals (i.e. administering the compounds to the animal once every month).

The present invention will now be described by way of the following non-limiting examples and figures, wherein.

EXAMPLES

1. Preparation of Polymorphs

Figure 14:
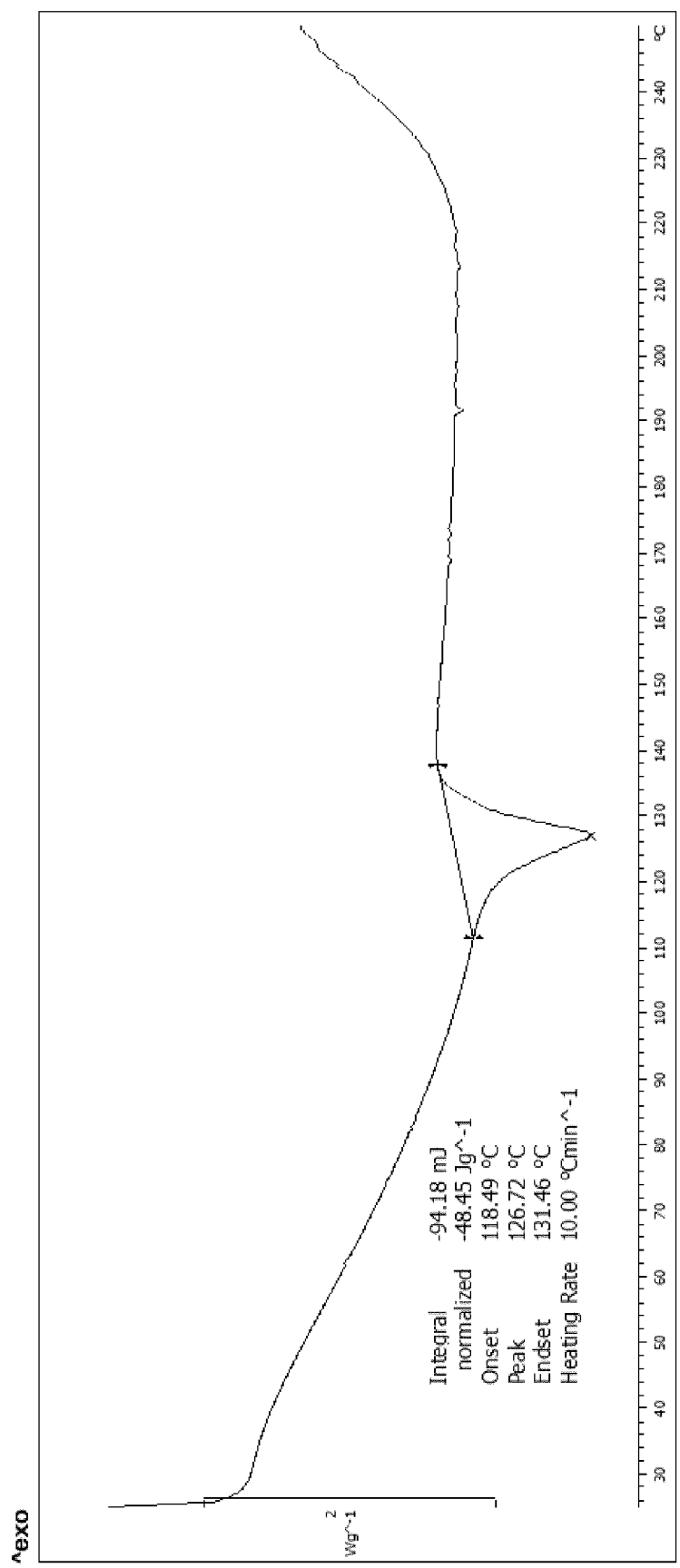
FIG. 14 shows a DSC trace of the polymorph designated Form A(c).

The compound of formula I was made by the methods described in WO 2011/067272. This resultant solid precipitate and liquid filtrate were analysed by HPLC as indicated in WO 2011/067272. The compound of formula IA was present in the filtrate and the compound of formula IC in the solid precipitate. When crystallised from the filtrate, the polymorph of Form A(c) was identified by DSC (see FIG. 14).

1a. Preparation of Form A(a)

Figure 1:
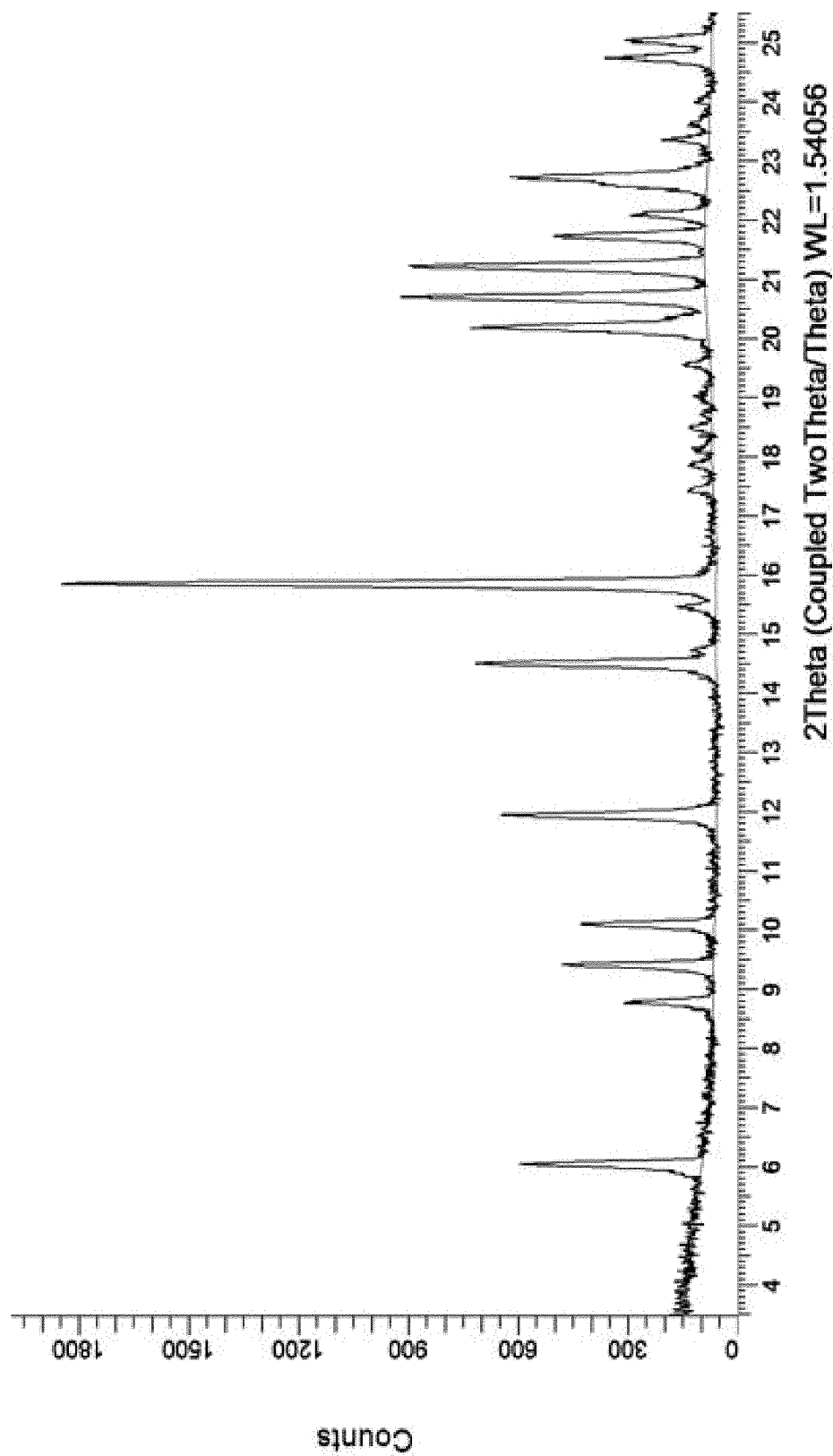
FIG. 1 shows the measured powder X-ray diffraction pattern of the polymorph designated Form A(a).
Figure 2:
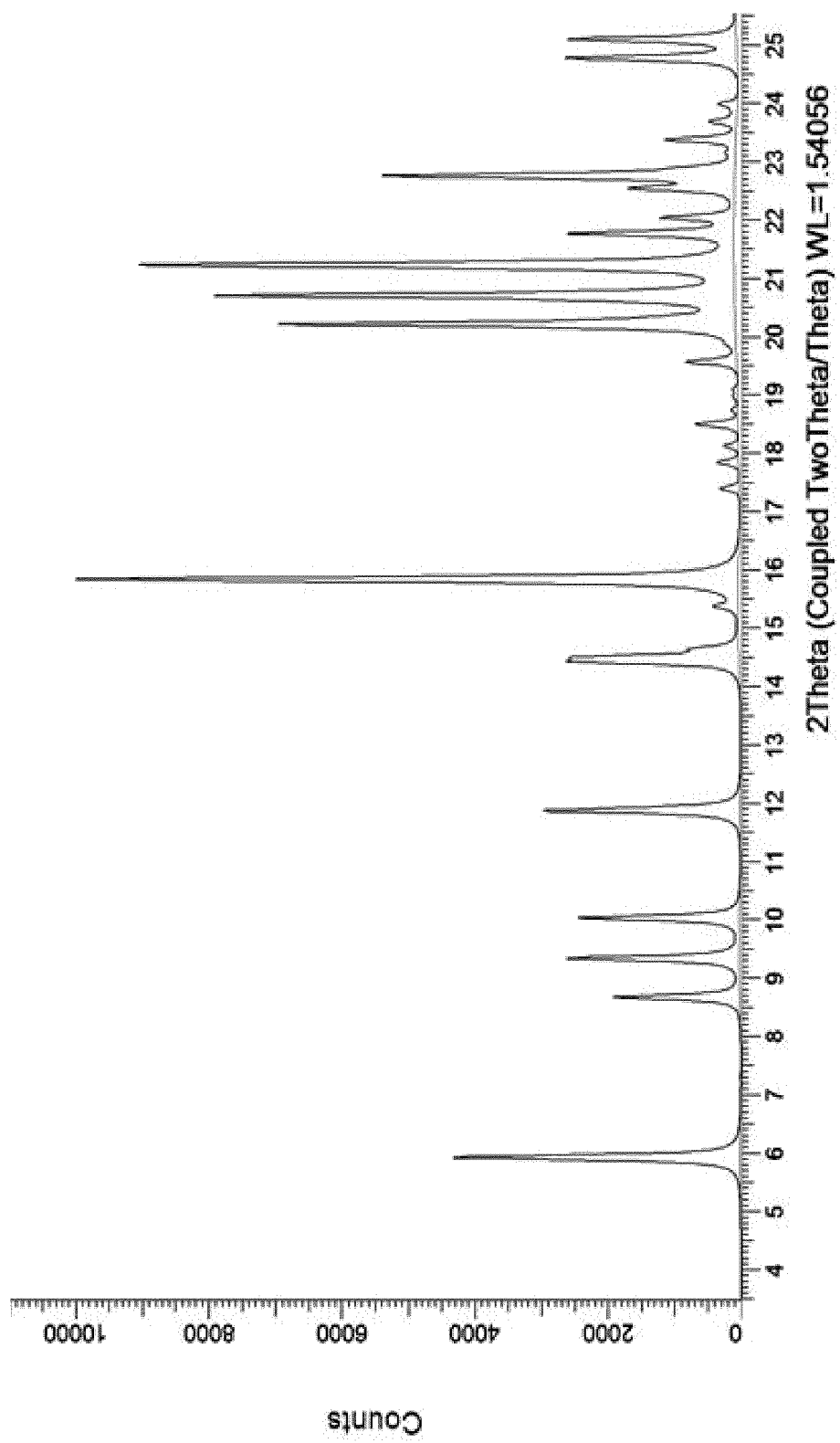
FIG. 2 shows the predicted powder X-ray diffraction pattern of the polymorph designated Form A(a).
Figure 3:
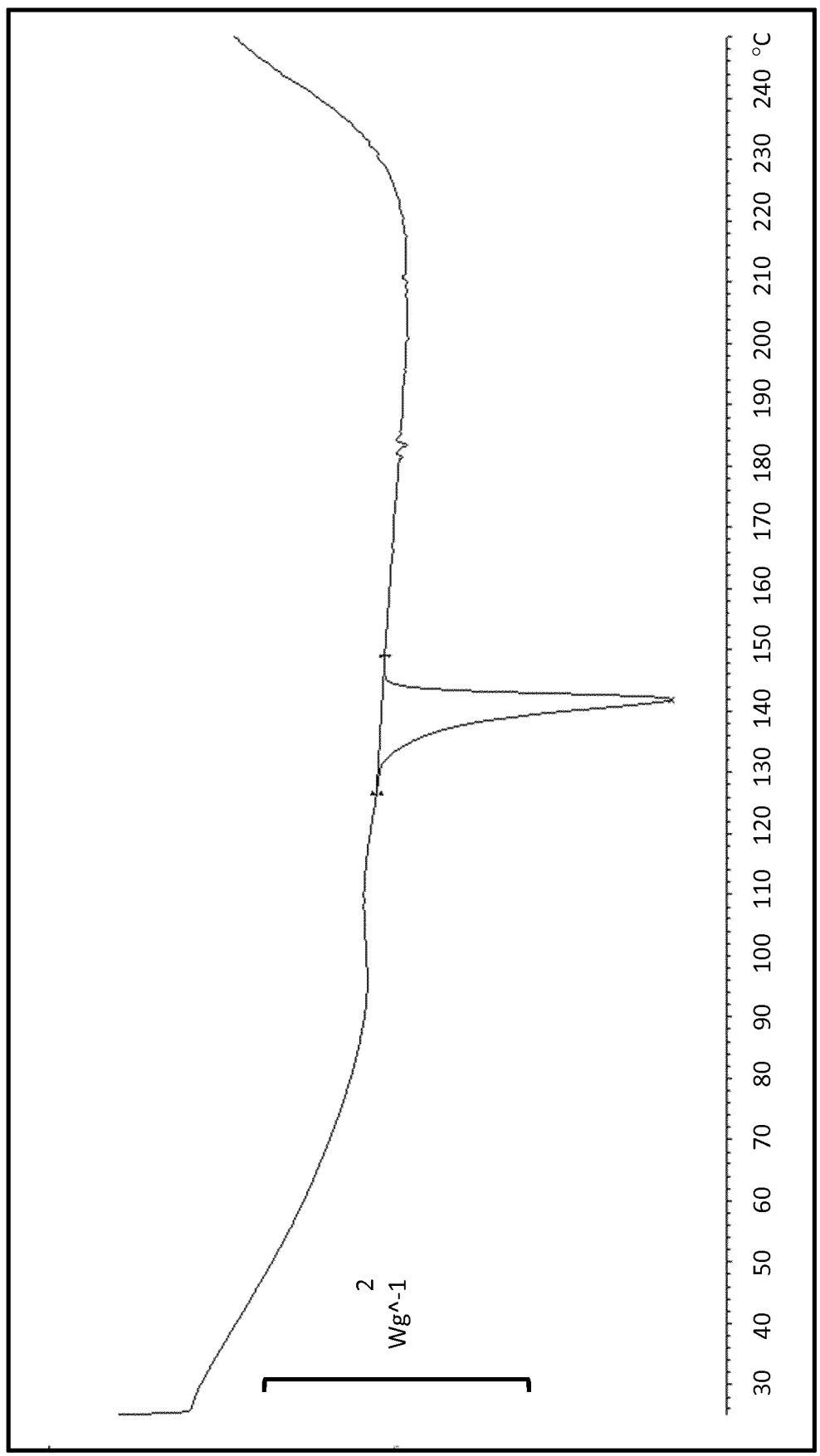
FIG. 3 shows a DSC trace of the polymorph designated Form A(a).

A purified sample of the compound of formula IA was slurried in dimethyl carbonate for 2 weeks at 25° C. after which crystals were isolated and characterised by DSC, powder X-ray diffraction and single crystal X-ray diffraction. A measured powder X-ray diffraction pattern for the polymorph of the compound of formula IA (designated Form A(a)) is shown in FIG. 1. The pattern predicted from the single crystal intensity data is show in FIG. 2. A DSC trace of of Form A(a) is shown in FIG. 3.

1b. Preparation of Form A(b)

Figure 4:
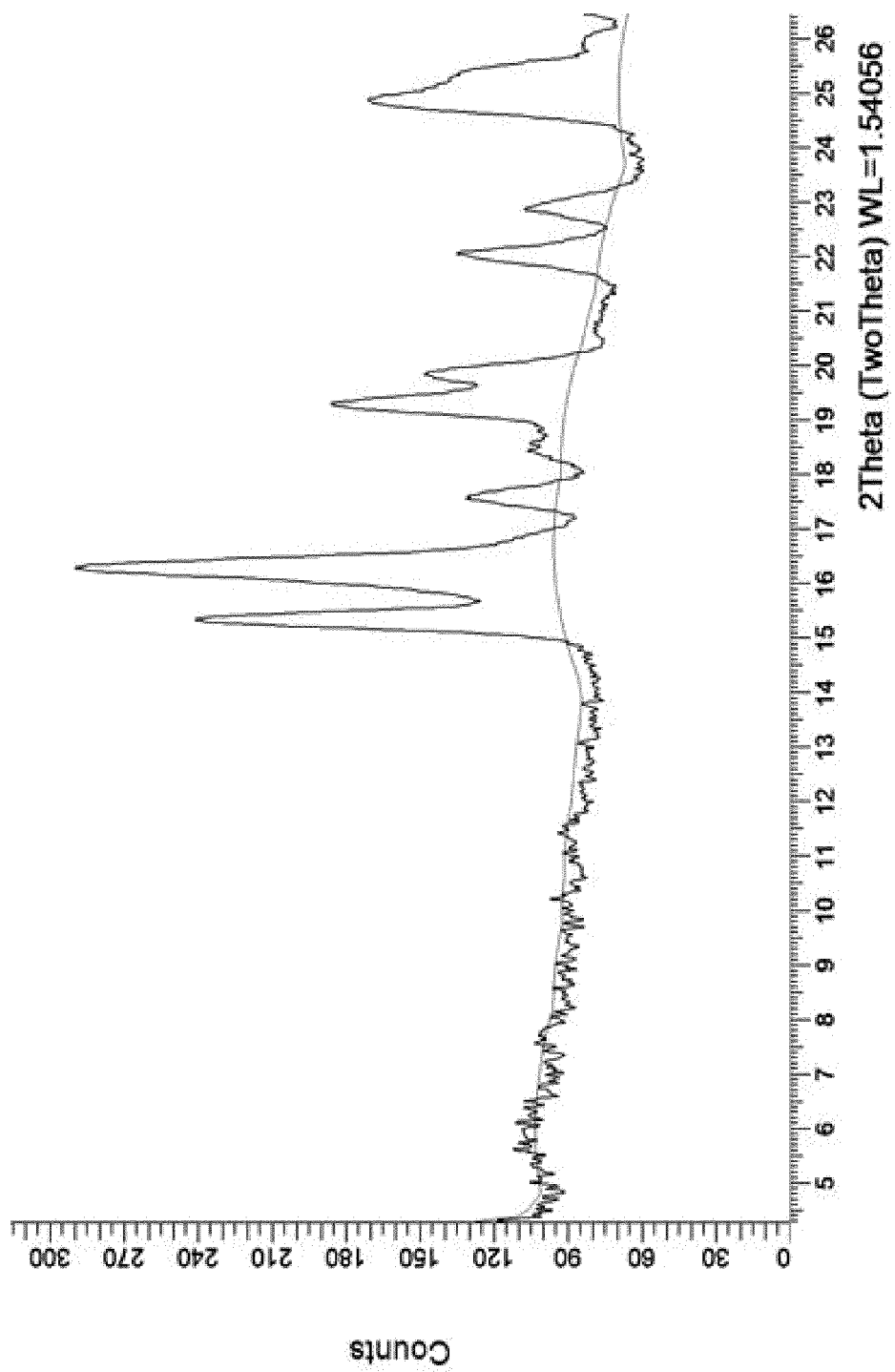
FIG. 4 shows the measured powder X-ray diffraction pattern of the polymorph designated Form A(b).
Figure 5:
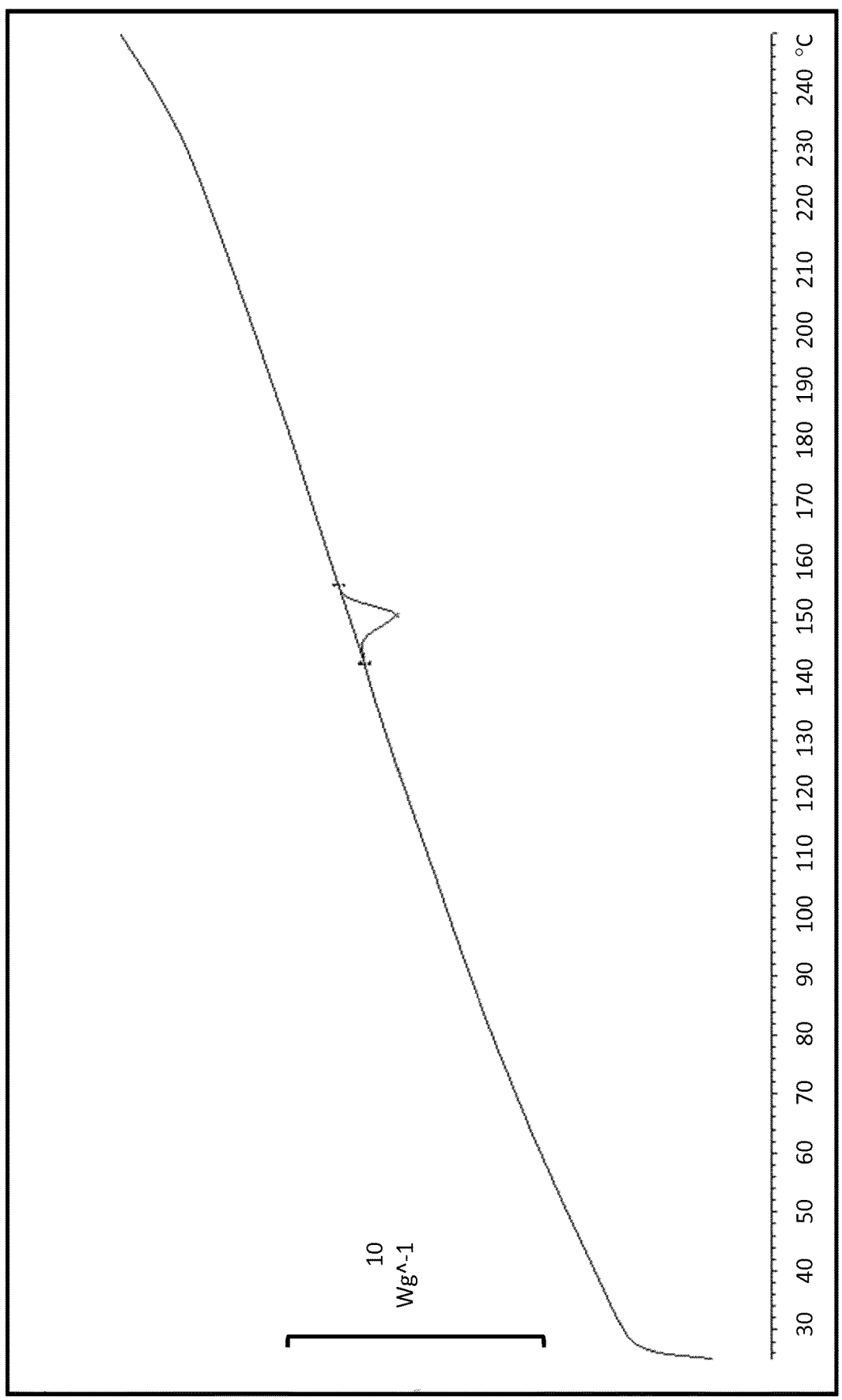
FIG. 5 shows a DSC trace of the polymorph designated Form A(b).

A further sample of the compound of formula IA was subject to slow evaporation at room temperature from a number of solvents. The sample isolated after evaporation from 20% water/methanol was analysed by DSC and powder X-ray diffraction. A measured powder X-ray diffraction pattern for the polymorph of the compound of formula IA (designated Form A(b)) is shown in FIG. 4. A DSC trace of Form A(b) is shown in FIG. 5.

1c. Preparation of Form A(h)

Figure 6:
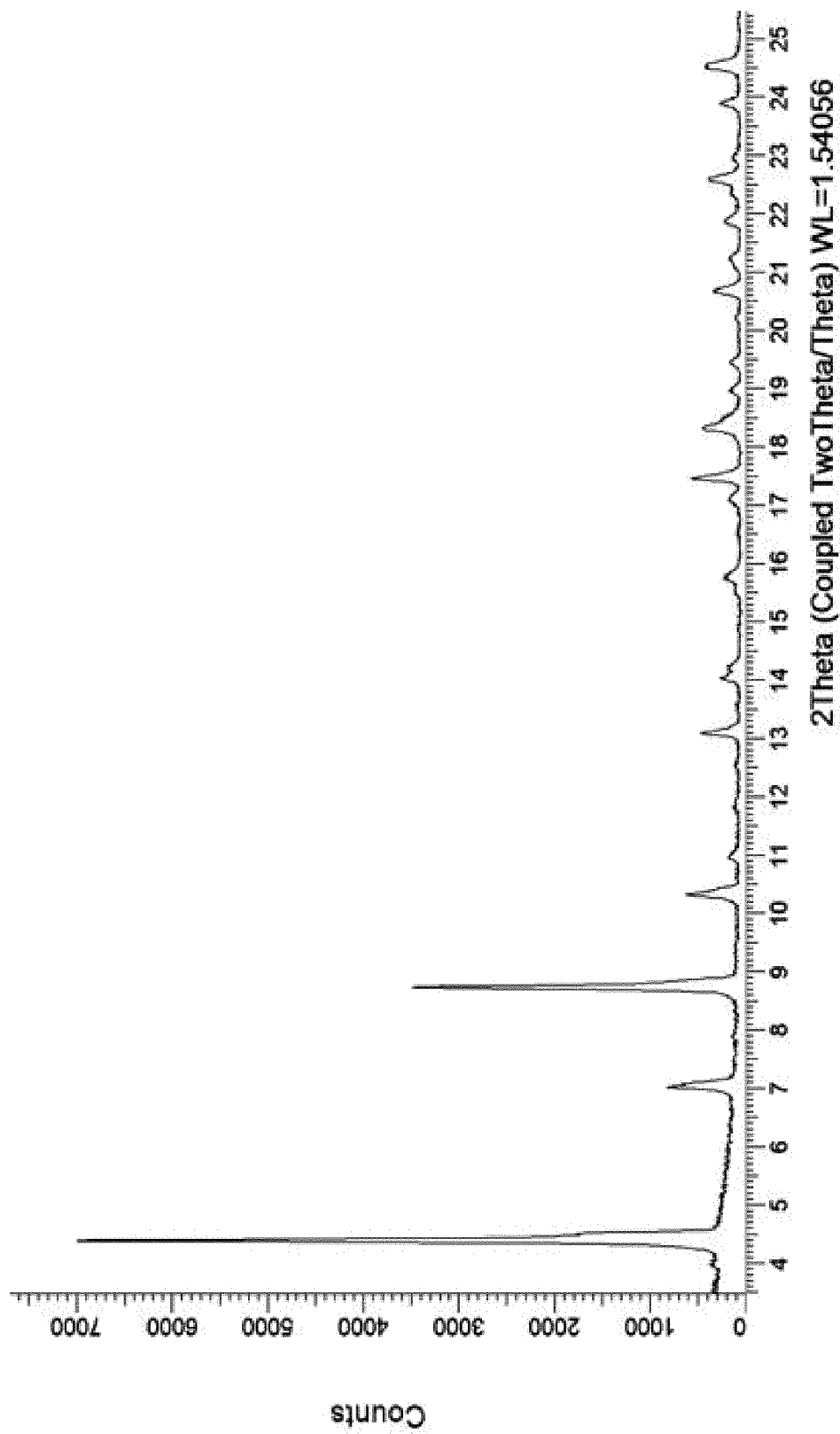
FIG. 6 shows the measured powder X-ray diffraction pattern of the hydrate of the compound of formula IA.
Figure 7:
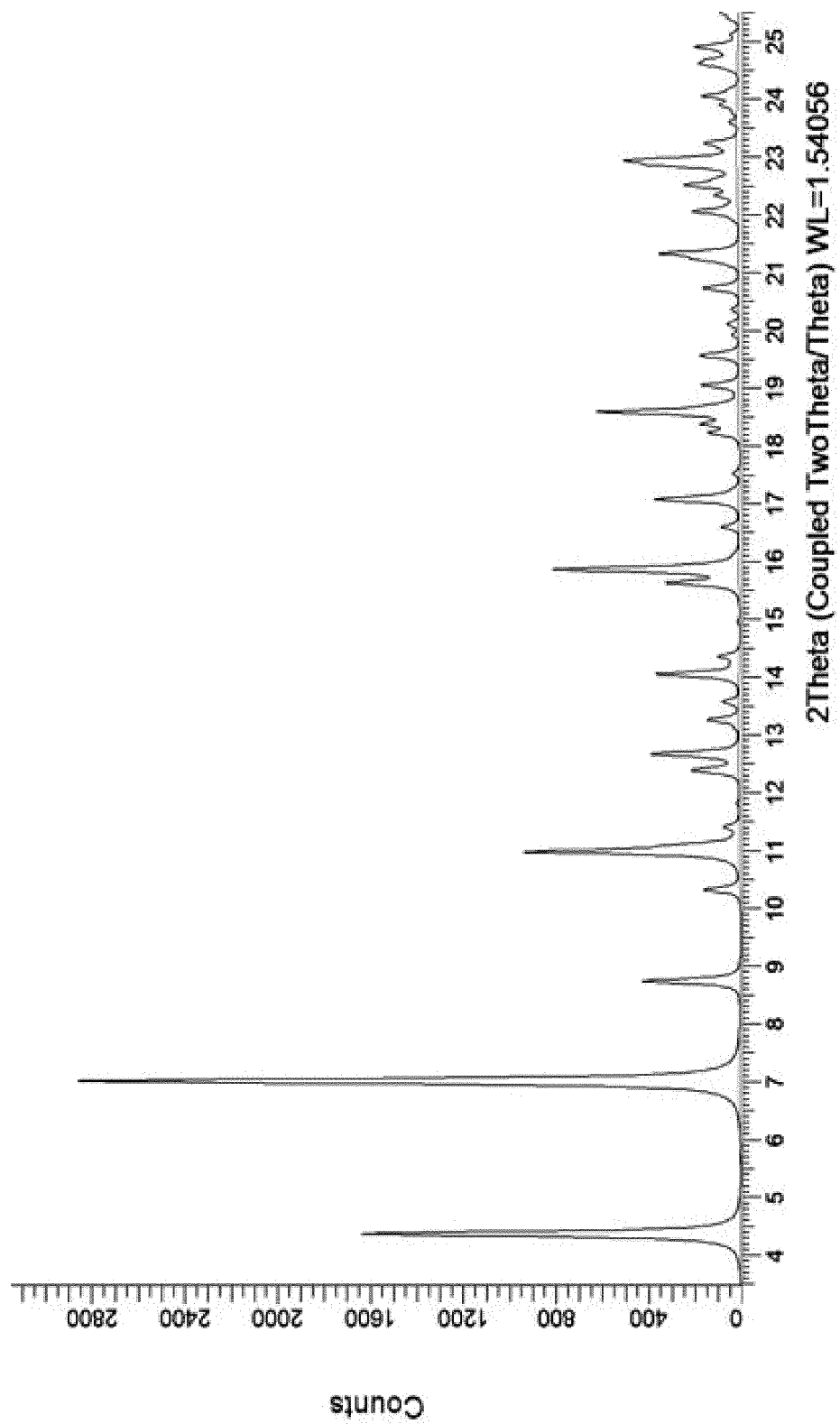
FIG. 7 shows the predicted powder X-ray diffraction pattern of the hydrate of the compound of formula IA.

A further sample of the compound of formula IA was subject to slow avaporation from a water/ethanol mix. Analysis of the crystals showed that water was incorporated in the structure—with two water molecules and two molecules of the compound of formula IA in the asymmetric unit. This hydrate (designated Form A(h)) was subject to analysis by DSC and TGA as well as powder X-ray diffraction and single crystal X-ray diffraction. A measured powder X-ray diffraction pattern for the hydrate is shown in FIG. 6. The pattern predicted from the single crystal intensity data is show in FIG. 7.

1d. Preparation of Form B(a) and Form C(a)

Figure 8:
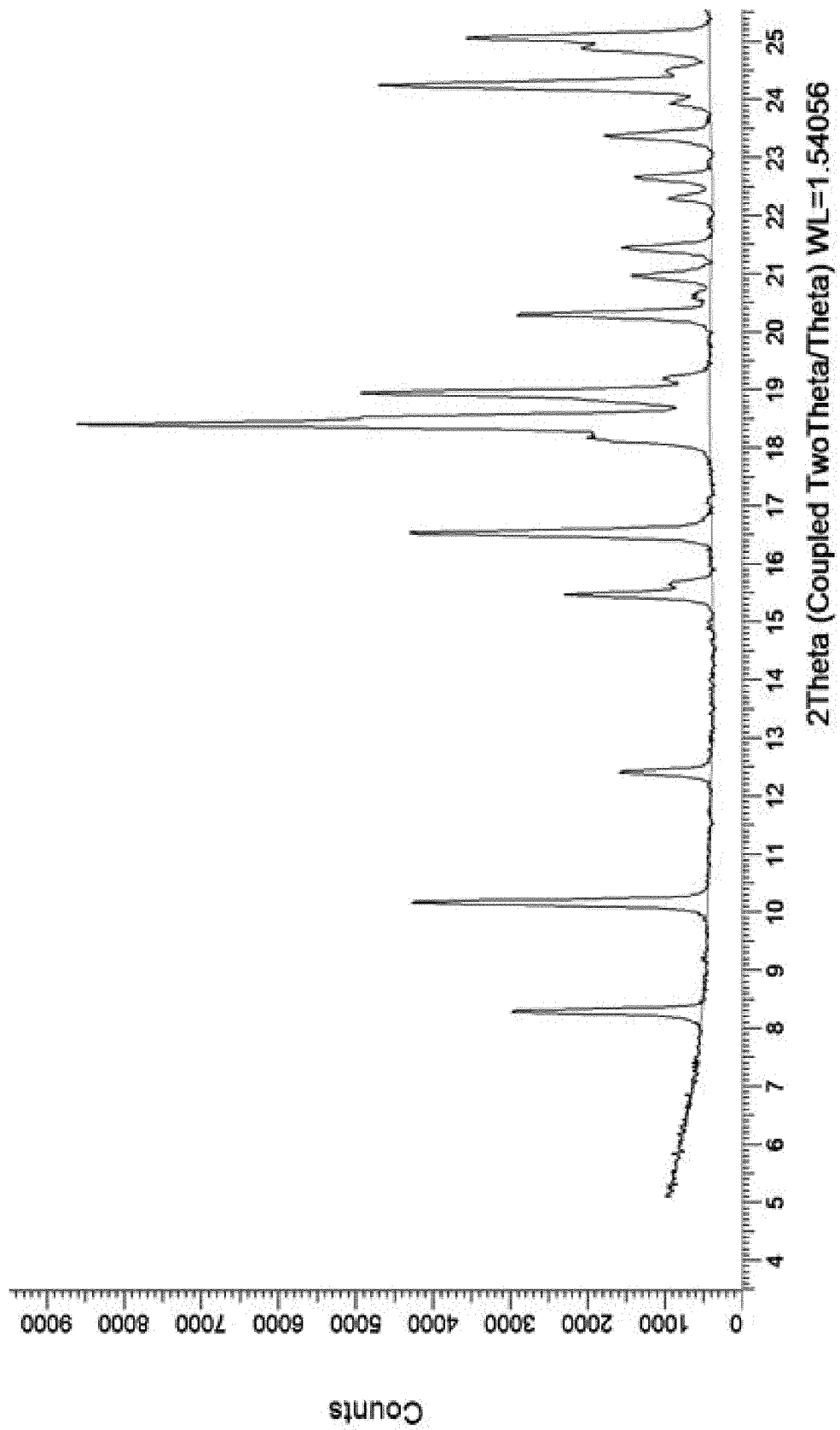
FIG. 8 shows the measured powder X-ray diffraction pattern of the polymorph of the compound of formula IB.
Figure 9:
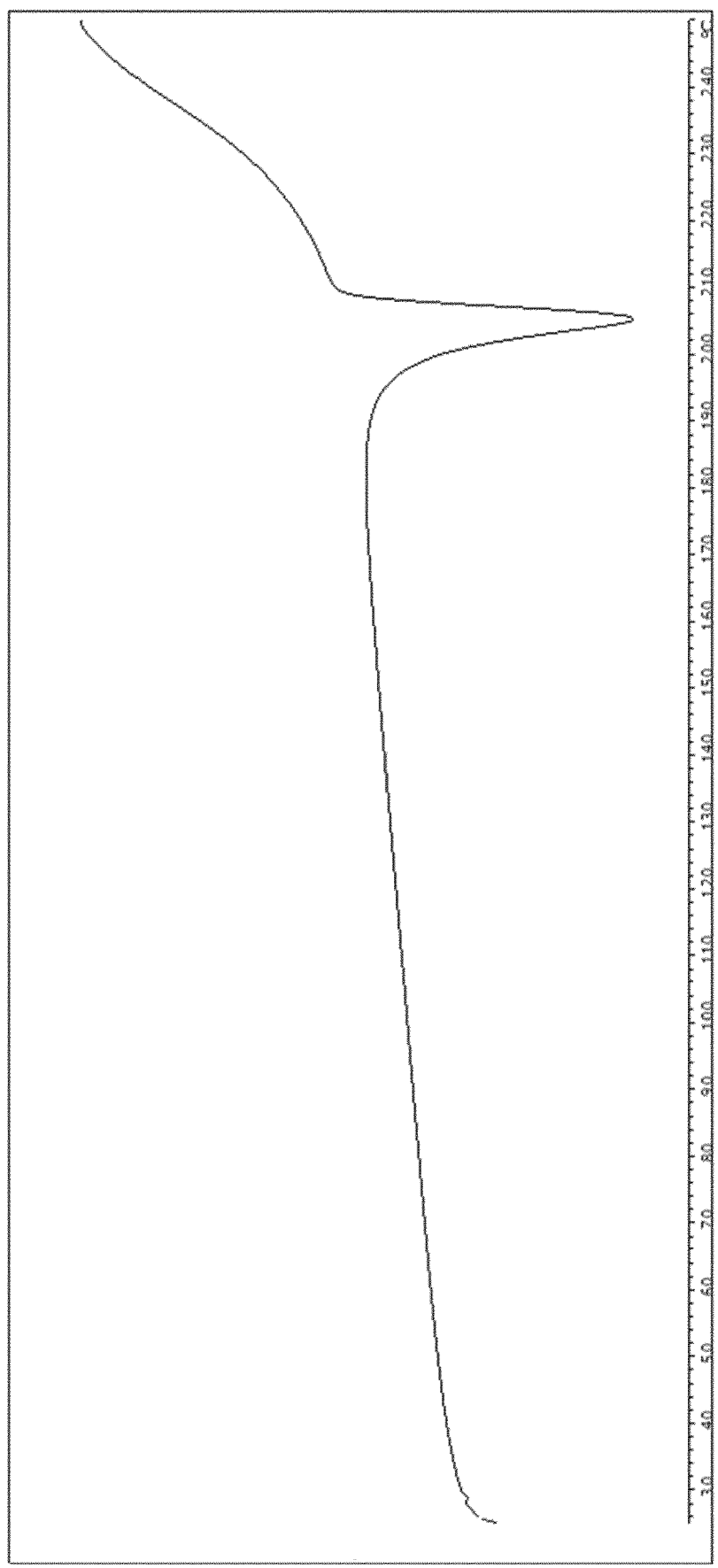
FIG. 9 shows a DSC trace of the polymorph of the compound of formula IB.

Samples of the compounds of formula IB and IC were prepared by dissolving the samples in acetone, filtering the acetone through a 0.2 μm syringe filter into a clean vial and leaving the vial in a fume cupboard to allow the acetone to evaporate. The resulting solid samples were analysed by powder X-ray diffraction and DSC. The powder X-ray diffraction patterns for IB and IC were identical. The pattern for the compound of formula IB is shown in FIG. 8. The DSC for this compound is shown in FIG. 9.

Figure 10:
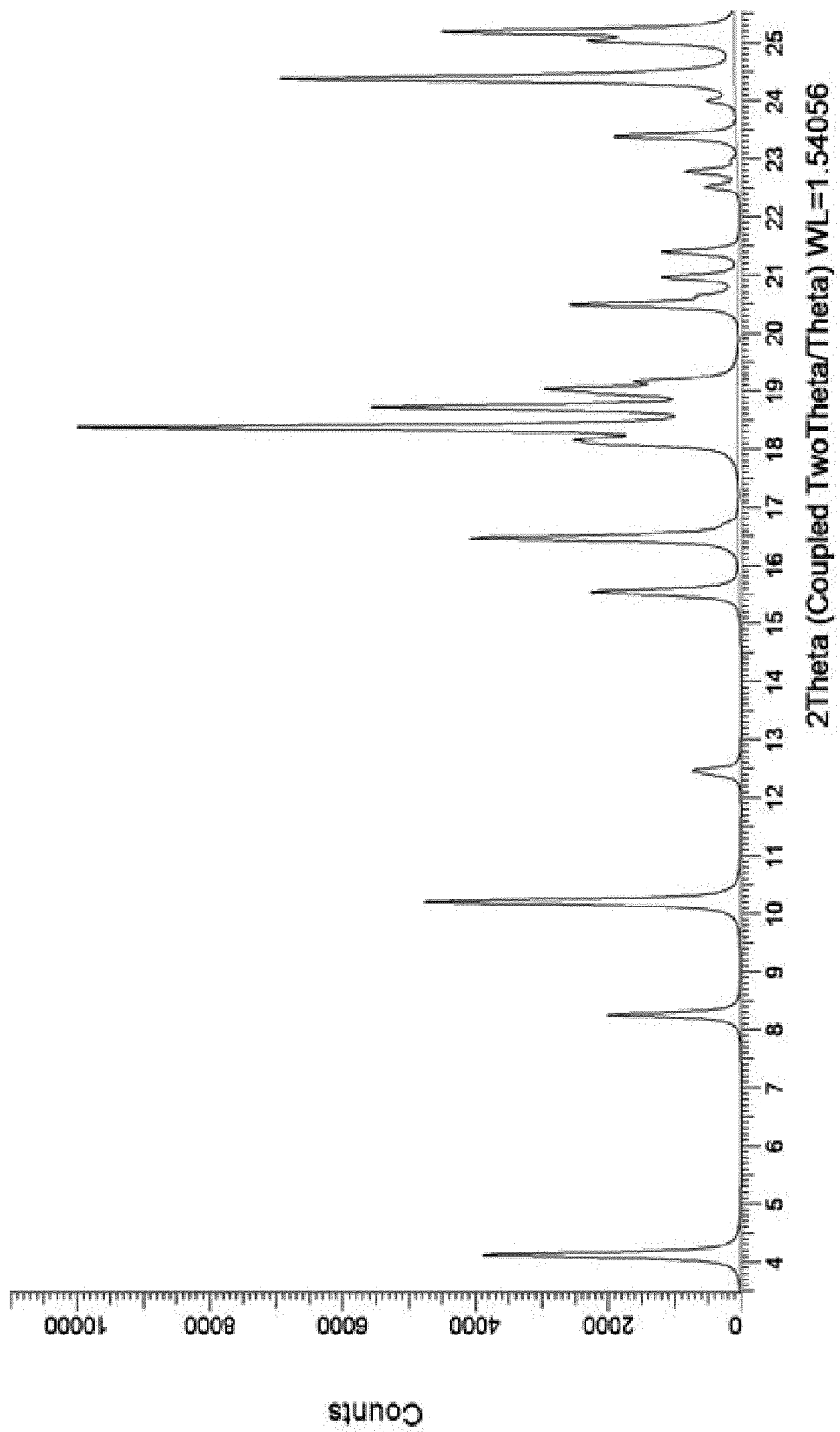
FIG. 10 shows the predicted powder X-ray diffraction pattern of the polymorph of the compound of formula IB.

Crystals suitable for single crystal X-ray diffraction analysis were grown in a mix of isopropanol/water (80/20). The pattern predicted from the single crystal intensity data is shown in FIG. 10.

1e. Preparation of a Racemic Mixture of the Compounds of Formula IA and ID

Figure 11:
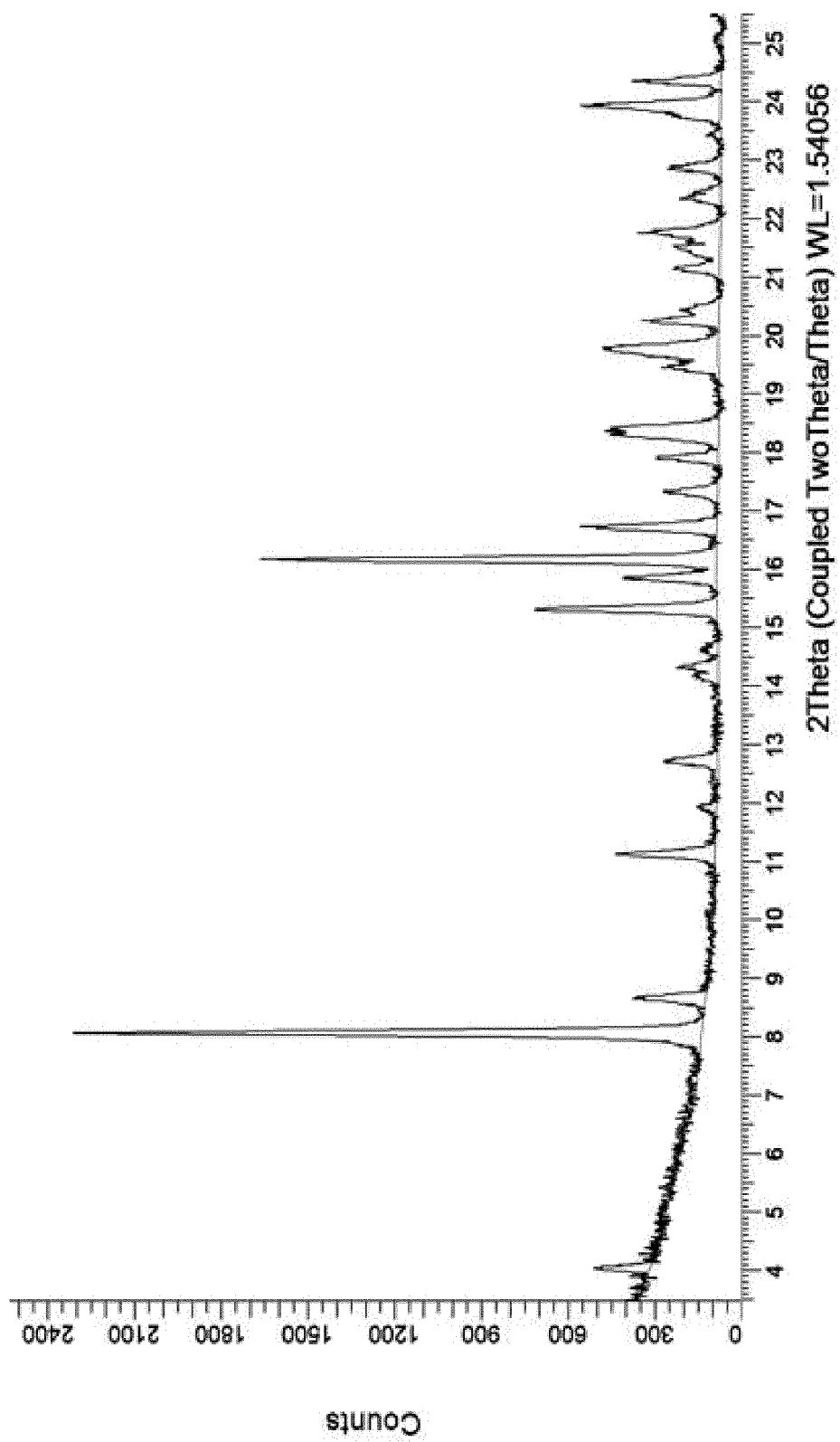
FIG. 11 shows the measured powder X-ray diffraction pattern of the polymorph of the racemate of the compounds of formula IA and ID.
Figure 12:
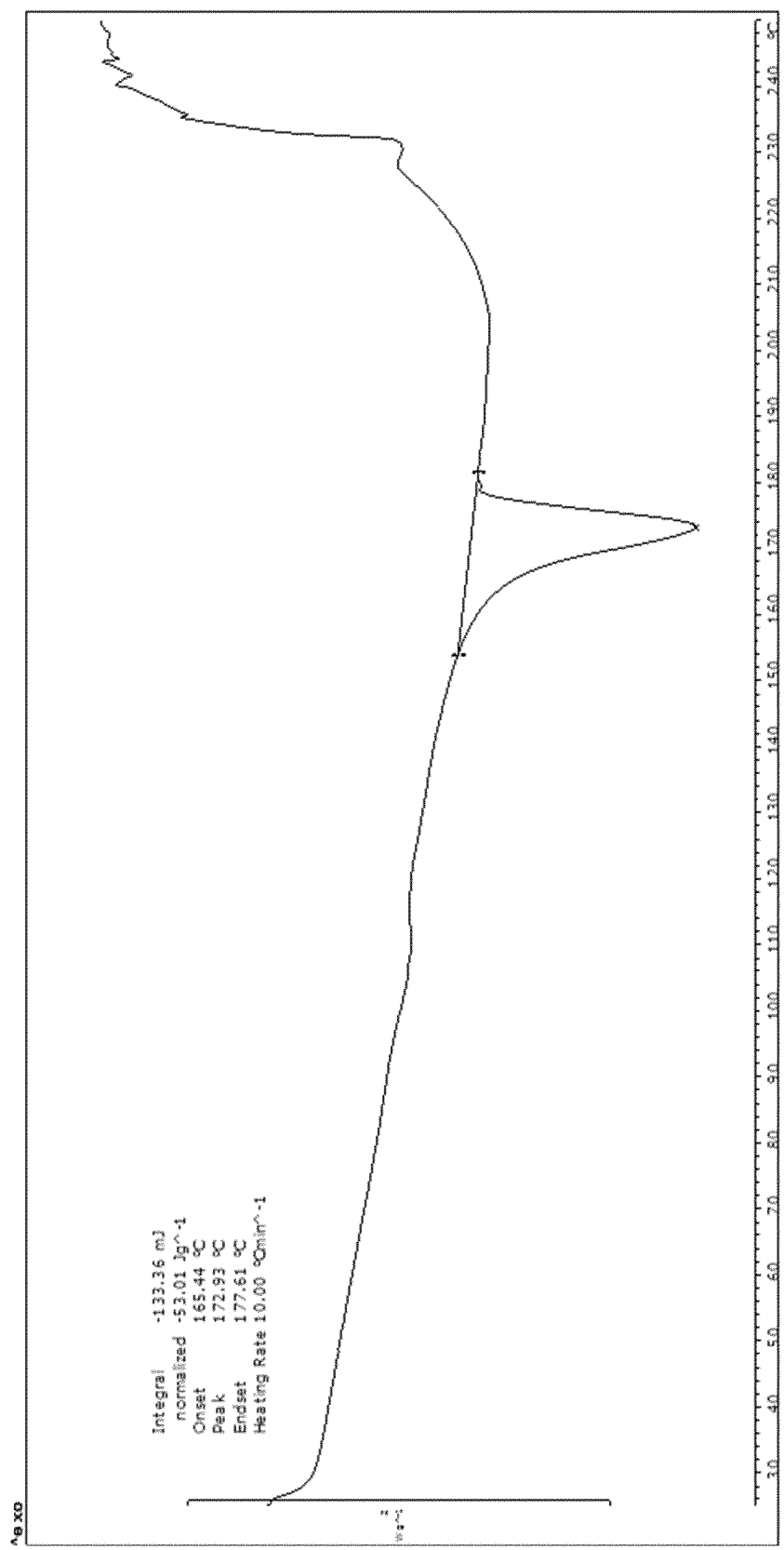
FIG. 12 shows a DSC trace of the polymorph of the racemate of the compounds of formula IA and ID.
Figure 13:
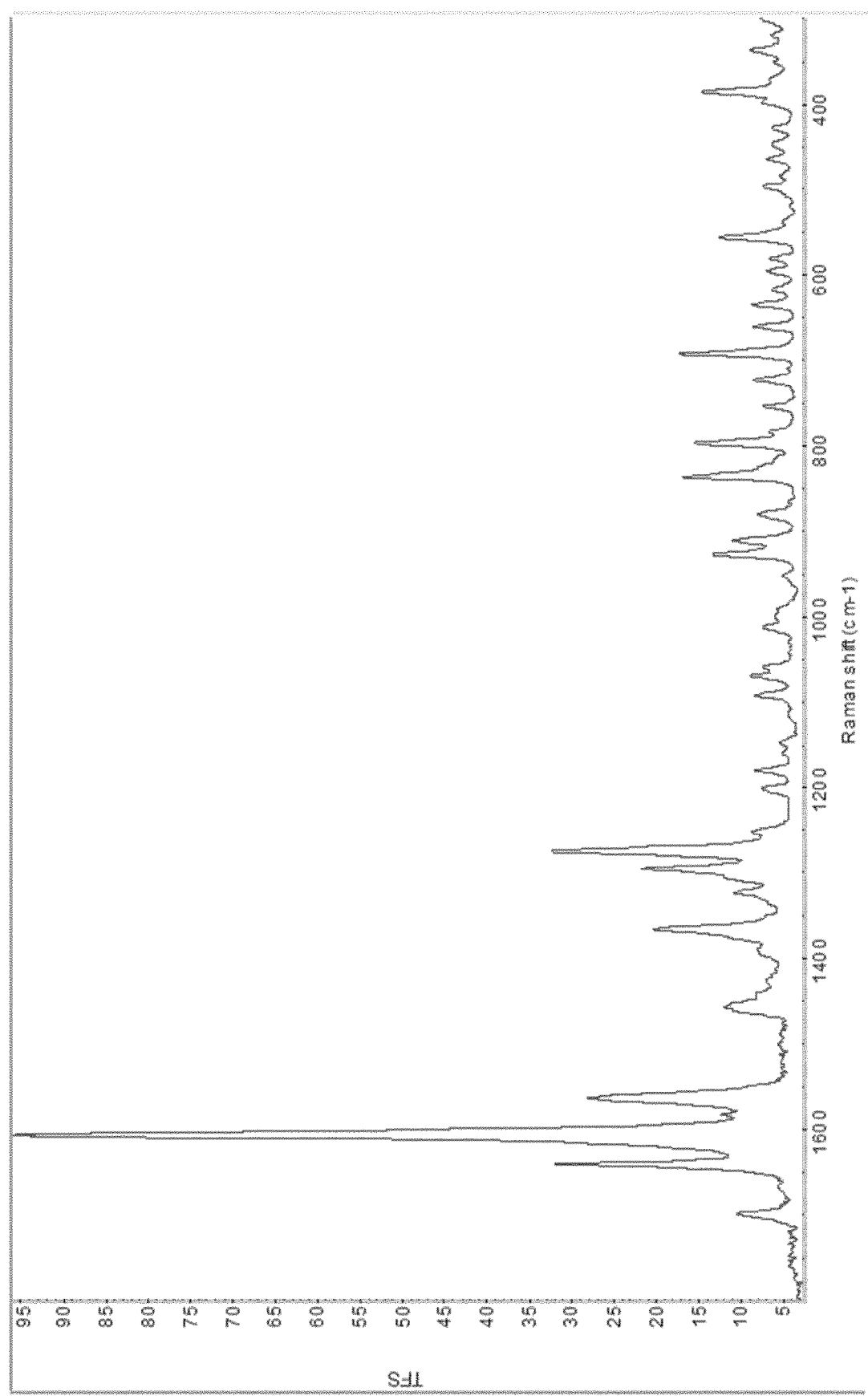
FIG. 13 shows a Raman spectra of the polymorph designated Form A(a).

Equal amounts of the compounds of formula IA and ID were dissolved in acetone and then left at room temperature until the solvent had evaporated. The resulting crystalline solid was characterised by powder X-ray diffraction and DSC. A measured powder X-ray diffraction pattern for the polymorph of the racemate of the compounds of formula IA and ID is shown in FIG. 11. A DSC trace of this polymorph is shown in FIG. 12.

2. Analysis of Polymorphs

After preparation, the samples were subject to analysis by powder X-ray diffraction and/or single crystal X-ray diffraction and/or differential scanning calorimetry (DSC) and/or thermal gravimetric analysis (TGA), as detailed above. The methods used for these analysis techniqes are detailed below:

Powder X-ray diffraction analysis of solid material was carried out using the Bruker D8 powder diffractometer at room temperature and at relative humidities above 40%. Samples were mounted in Perspex sample holders and the samples flattened. The sample holder was rotated and X-rays were collected from 4° to 34° 2-theta, with a scan time of 25 to 30 minutes depending on the pattern intensity.

Single crystal intensity data was collected on an Oxford Xcalibar PX Ultra diffractometer using Cu Kα radiation (λ=1.5418 Å) with a graphite monochromator. The crystal was mounted in Paratone N oil at 100K for data collection. The data was solved using the CRYSTALS software package.

DSC was carried out using a Mettler Toledo DSC1. A sample loading of around 5 mg was used and this was heated from 25° C. to 160° C. at a rate of 10° C./minute. The lid of the DSC crucible was pierced to allow the escape of any gas formed during the heating of the sample.

Raman spectroscopy was carried out using a Thermo Scientific DXR Raman microscope: a 780 nM Raman laser was focused on the sample on a quartz slide.

3. Stability of Polymorphs

A sample of the polymorph designated Form A(c) was stirred in 5 ml dimethyl carbonate for two days. The crystals were isolated, air dried and characterised by DSC and pXRD. The DSC curve showed a sharp single melting endotherm with a melting peak at 141° C. and the pXRD pattern matched that of Form A(a), indicating that all of the Form A(c) had converted into Form (A)a.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. All publications cited herein are hereby incorporated by reference in their entirety for all purposes to the same extent as if each individual publication were specifically and individually indicated to be so incorporated by reference.

What is claimed is:

1. A crystalline polymorph of the compound of formula IA

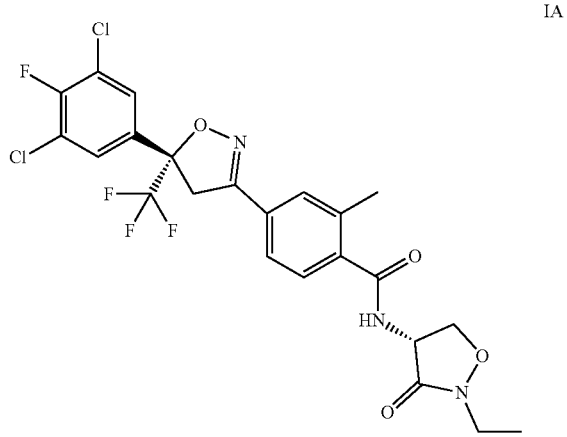 [SMILES: CCN1OC[C@@H](NC(=O)c2ccc(C3=NO[C@@](c4cc(Cl)c(F)c(Cl)c4)(C(F)(F)F)C3)cc2C)C1=O]

which has a powder X-ray diffraction pattern comprising at least three 2θ angle values selected from the group consisting of 6.0±0.2, 8.8±0.2, 9.4±0.2, 10.1±0.2, 11.9±0.2, 14.5±0.2, 15.9±0.2, 20.2±0.2, 20.7±0.2, 21.2±0.2, 21.7±0.2, 22.1±0.2 and 22.7±0.2.

2. The crystalline polymorph of claim 1, which has the following lattice parameters: a=5.06 Å±0.01 Å, b=18.92 Å±0.01 Å, c=24.17 Å±0.01 Å, α=90°±0.01°, β=90°±0.01°, γ=90°±0.01° and volume=2315 Å³±1 Å³.

3. The crystalline polymorph of claim 1, which has a melting point of 141° C.±2° C.

4. A crystalline polymorph of the compound of formula IA,

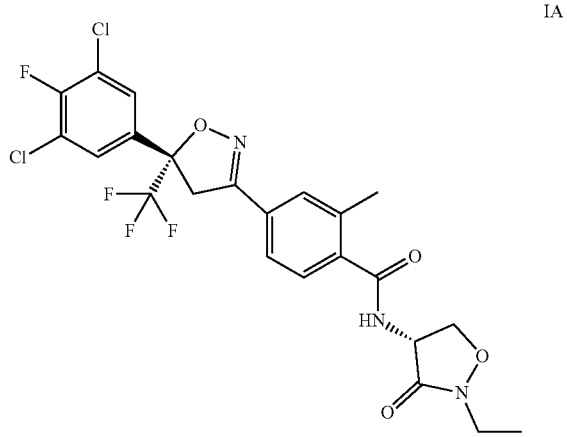 [SMILES: CCN1OC[C@@H](NC(=O)c2ccc(C3=NO[C@@](c4cc(Cl)c(F)c(Cl)c4)(C(F)(F)F)C3)cc2C)C1=O]

which is a hydrate and which has a powder X-ray diffraction pattern comprising at least three 2θ angle values selected from the group consisting of 4.4±0.2, 7.0±0.2, 8.7±0.2, 10.3±0.2, 11.0±0.2, 12.4±0.2, 12.7±0.2, 13.3±0.2, 14.1±0.2, 15.9±0.2, 17.1±0.2, 18.6±0.2, 19.0±0.2 and 19.6±0.2.

5. The crystalline polymorph of claim 4, which has the following lattice parameters: a=8.03 Å±0.01 Å, b=16.10 Å±0.01 Å, c=20.37 Å±0.01 Å, α=90°±0.01°, β=97.02°±0.01°, γ=90°±0.01° and volume=2615 Å³±1 Å³.

6. A crystalline polymorph of the compound of formula IB or IC

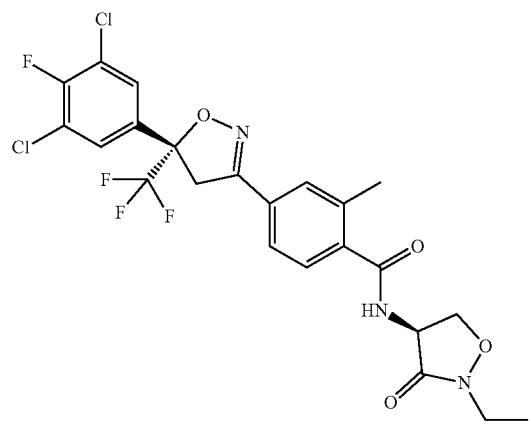
(IB)

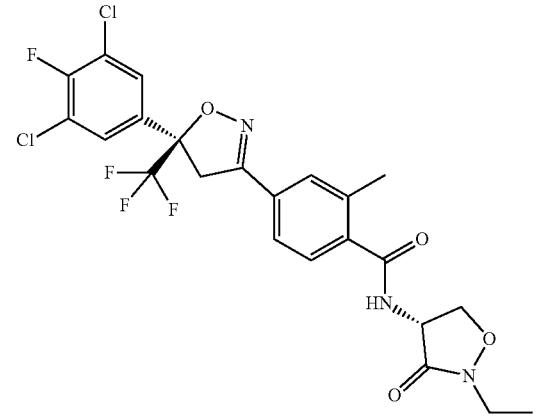
(IC)

which has a powder X-ray diffraction pattern comprising at least three 2θ angle values selected from the group consisting of 4.1±0.2, 8.3±0.2, 10.2±0.2, 12.4±0.2, 15.5±0.2, 16.5±0.2, 18.2±0.2, 18.4±0.2, 18.7±0.2, 19.0±0.2, 20.5±0.2, 21.0±0.2 and 21.4±0.2.

7. The crystalline polymorph of claim 6, which has a melting point of 206° C.±2° C.

8. A crystalline polymorph of the racemate of the compounds of formula IA and

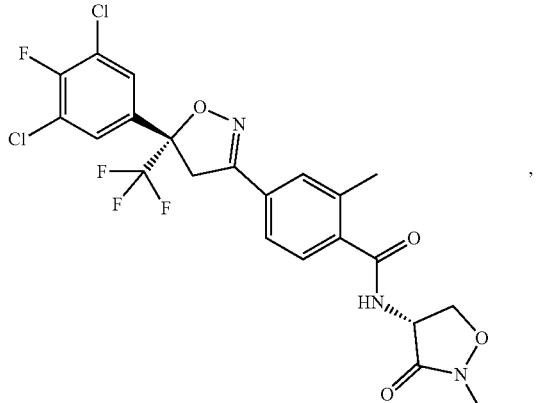
(IA)

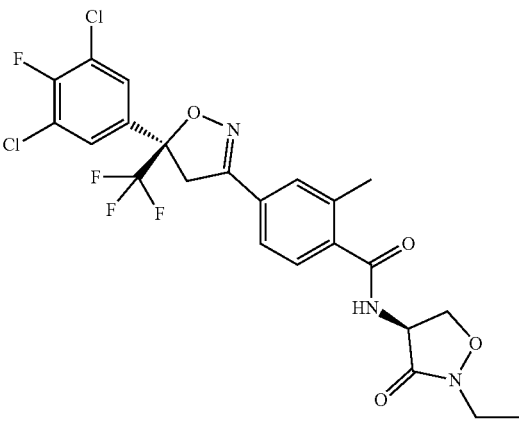
(ID)

which has a powder X-ray diffraction pattern comprising at least three 2θangle values selected from the group consisting of 4.0±0.2, 8.1±0.2, 9.7±0.2, 11.1±0.2, 12.7±0.2, 15.3±0.2, 15.9±0.2, 16.2±0.2, 16.7±0.2, 18.4±0.2, 19.5±0.2, 19.8±0.2, 20.3±0.2, 21.8±0.2 and 23.9±0.2.

9. The crystalline polymorph of claim 8, which has a melting point of 173° C.±2° C.

10. An agricultural composition comprising a polymorph as claimed in claim 1 and at least one agriculturally acceptable carrier or diluent.

11. The composition of claim 10, which further comprises a polymorph of the compound of formula IB or IC

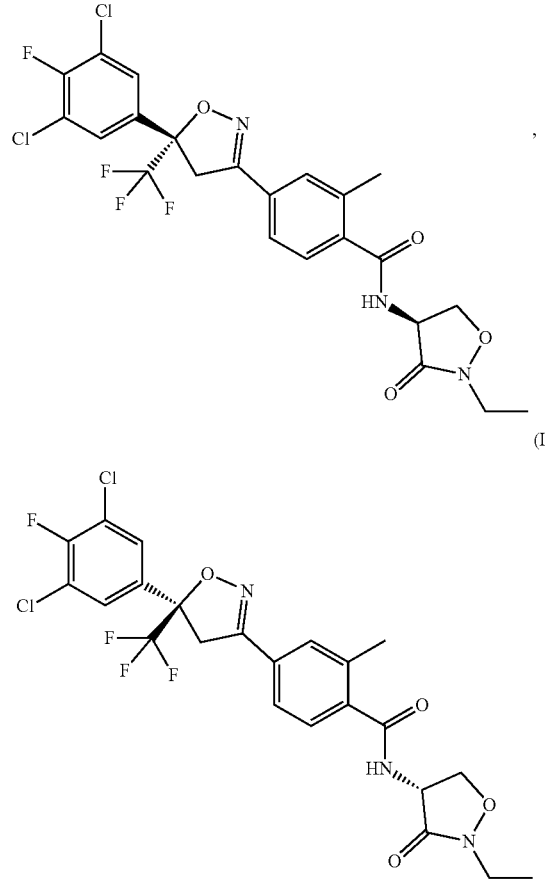

or a polymorph of the racemate of the compounds of formula IA and ID

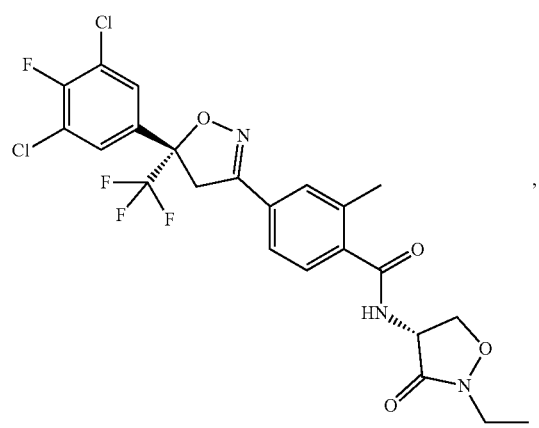

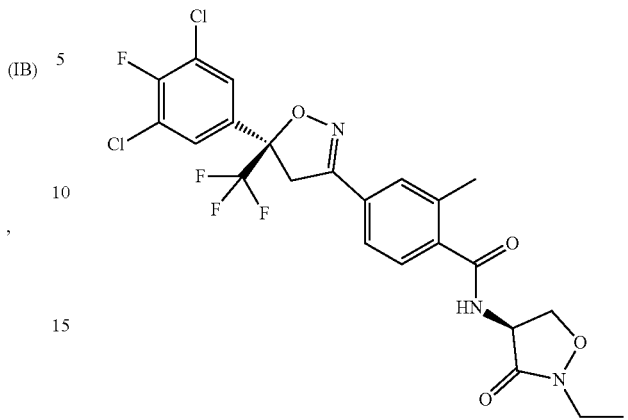

12. The composition of claim 10, which is enriched for a polymorph of the compound of formula IA.

13. The composition of claim 12, wherein the polymorph of the compound of formula IA has the following lattice parameters: a=5.06 Å±0.01 Å, b=18.92 Å±0.01 Å, c=24.17 Å±0.01 Å, α=90°±0.01°, β=90°±0.01°, γ90°±0.01° and volume=2315 Å³±1 Å³.

14. The composition of claim 10, which comprises at least one further insecticide or nematicide.

15. A method of preventing or controlling insect infection on plants or plant propagation material comprising treating the plant or plant propagation material with an insecticidally effective amount of an agricultural composition as claimed in claim 10.

16. An agricultural composition comprising a polymorph as claimed in claim 6 and at least one agriculturally acceptable carrier or diluent.

17. A method of preventing or controlling insect infection on plants or plant propagation material comprising treating the plant or plant propagation material with an insecticidally effective amount of an agricultural composition as claimed in claim 16.

18. An agricultural composition comprising a polymorph as claimed in claim 8 and at least one agriculturally acceptable carrier or diluent.

19. A method of preventing or controlling insect infection on plants or plant propagation material comprising treating the plant or plant propagation material with an insecticidally effective amount of an agricultural composition as claimed in claim 18.

20. The composition of claim 11, wherein:
the polymorph of the compound of formula IB or IC has a powder X-ray diffraction pattern comprising at least three 2θ angle values selected from the group consisting of 4.1±0.2, 8.3±0.2, 10.2±0.2, 12.4±0.2, 15.5±0.2, 16.5±0.2, 18.2±0.2, 18.4±0.2, 18.7±0.2, 19.0±0.2, 20.5±0.2, 21.0±0.2 and 21.4±0.2; and
the polymorph of the racemate of the compounds of formula IA and ID has a powder X-ray diffraction pattern comprising at least three 2θ angle values selected from the group consisting of 4.0±0.2, 8.1±0.2, 9.7±0.2, 11.1±0.2, 12.7±0.2, 15.3±0.2, 15.9±0.2, 16.2±0.2, 16.7±0.2, 18.4±0.2, 19.5±0.2, 19.8±0.2, 20.3±0.2, 21.8±0.2 and 23.9±0.2.

* * * * *